United States Patent
Shin et al.

(10) Patent No.: US 10,221,418 B2
(45) Date of Patent: Mar. 5, 2019

(54) COMPOSITION FOR TREATING CANCER ASSOCIATED WITH HPV INFECTION

(71) Applicant: EnhancedBio Inc., Seoul (KR)

(72) Inventors: Young Kee Shin, Seoul (KR); Young Deug Kim, Incheon (KR); Hun Soon Jung, Seoul (KR); Deuk Ae Kim, Seoul (KR)

(73) Assignee: EnhancedBio Inc., Seoul (KR)

( * ) Notice: Subject to any disclaimer, the term of this patent is extended or adjusted under 35 U.S.C. 154(b) by 0 days.

(21) Appl. No.: 15/632,600

(22) Filed: Jun. 26, 2017

(65) Prior Publication Data

US 2018/0044679 A1 Feb. 15, 2018

Related U.S. Application Data

(62) Division of application No. 14/419,234, filed as application No. PCT/KR2013/006963 on Aug. 1, 2013, now Pat. No. 9,719,093.

(30) Foreign Application Priority Data

Aug. 2, 2012 (KR) ........................ 10-2012-0084820

(51) Int. Cl.
| | | |
|---|---|---|
| A61K 48/00 | (2006.01) | |
| C12N 15/113 | (2010.01) | |
| A61K 31/7105 | (2006.01) | |
| A61K 31/713 | (2006.01) | |
| A61K 31/7088 | (2006.01) | |

(52) U.S. Cl.
CPC ...... *C12N 15/1131* (2013.01); *A61K 31/7088* (2013.01); *A61K 31/713* (2013.01); *A61K 31/7105* (2013.01); *A61K 48/00* (2013.01); *C12N 2310/11* (2013.01); *C12N 2310/122* (2013.01); *C12N 2310/14* (2013.01); *C12N 2310/321* (2013.01); *C12N 2310/322* (2013.01); *C12N 2310/334* (2013.01); *C12N 2310/335* (2013.01); *C12N 2310/336* (2013.01); *C12N 2310/3521* (2013.01); *C12N 2310/3533* (2013.01); *C12N 2310/531* (2013.01)

(58) Field of Classification Search
CPC ..................................................... A61K 48/00
See application file for complete search history.

(56) References Cited

U.S. PATENT DOCUMENTS

| 6,583,278 | B1 | 6/2003 | Carter |
| 7,691,997 | B2 | 4/2010 | Khvorova et al. |
| 7,732,166 | B2 | 6/2010 | Cheng |
| 7,956,177 | B2 * | 6/2011 | Benson ................. C12N 15/111 |
| | | | 435/325 |
| 8,377,899 | B2 | 2/2013 | Shin et al. |

| 2004/0198640 | A1 | 10/2004 | Leake et al. |
| 2009/0324584 | A1 | 12/2009 | Hoerr et al. |
| 2010/0254944 | A1 | 10/2010 | Subramanian et al. |
| 2011/0269814 | A1 | 11/2011 | Manoharan et al. |

FOREIGN PATENT DOCUMENTS

| CN | 101410518 A | 4/2009 |
| JP | 2003-500481 A | 1/2003 |
| JP | 2004-535813 A | 12/2004 |
| JP | 2006-504427 A | 2/2006 |
| JP | 2006-320327 A | 11/2006 |
| JP | 2009-531433 A | 9/2009 |
| KR | 10-2008-0040412 A | 5/2008 |
| KR | 10-2009-0064453 A | 6/2009 |
| KR | 10-2011-0084650 A | 7/2011 |
| RU | 2487938 C2 | 7/2013 |
| WO | WO-03/008573 A2 | 1/2003 |
| WO | WO-2004/011647 A1 | 2/2004 |
| WO | WO-2004/039957 A2 | 5/2004 |
| WO | WO-2007/111998 A2 | 10/2007 |
| WO | WO-2008/054184 A1 | 5/2008 |
| WO | WO-2008/139938 A1 | 11/2008 |
| WO | WO-2008/156702 A2 | 12/2008 |
| WO | WO-2010/057009 A1 | 5/2010 |
| WO | WO-2010/129941 A1 | 11/2010 |
| WO | WO-2011/087343 A2 | 7/2011 |
| WO | WO-2012/016139 A2 | 2/2012 |

OTHER PUBLICATIONS

Judge, Adam D., et al. "Design of noninflammatory synthetic siRNA mediating potent gene silencing in vivo." Molecular Therapy 13.3 (2006): 494-505.*
Jonson et al., "Gene silencing with siRNA targeting E6/E7 as a therapeutic intervention in a mouse model of cervical cancer," Gynecol Oncol. 111(2):356-64 (2008).
Jung et al., "The synergistic therapeutic effect of cisplatin with Human papillomavirus E6/E7 short interfering RNA on cervical cancer cell lines in vitro and in vivo," Int J Cancer. 130(8):1925-36 (2012).
Khairuddin et al., "siRNA-induced immunostimulation through TLR7 promotes antitumoral activity against HPV-driven tumors in vivo," Immunol Cell Biol. 90(2):187-96 (2012).
Notice of Allowance dated Jun. 27, 2017 for Russian Application No. 2015106855, Shin et al., "Composition for Treating Cancer Associated with HPV Infection," filed Aug. 1, 2013 (10 pages).

(Continued)

*Primary Examiner* — Kimberly Chong
(74) *Attorney, Agent, or Firm* — Clark & Elbing LLP; Susan M. Michaud

(57) ABSTRACT

The present invention relates to a composition for preventing or treating diseases associated with human papillomavirus (HPV), and more specifically, cancer associated with HPV, and even more specifically, cervical cancer. The nucleotide sequence of the present invention, the sequence in which the base thereof is modified, and a specific combination thereof can be useful in a composition for effectively treating diseases associated with HPV infection by greatly inhibiting the expression of the E6/E7 gene of HPV type 16 or 18.

4 Claims, 12 Drawing Sheets

Specification includes a Sequence Listing.

(56) References Cited

OTHER PUBLICATIONS

Office Action dated Apr. 24, 2017 for European Application No. 16204495.2, Shin et al., "Composition for Treating Cancer Associated with HPV Infection," filed Aug. 1, 2013 (14 pages).
Office Action dated Feb. 21, 2017 for Japanese Application No. 2016-086754, Shin et al., "Composition for Treating Cancer Associated with HPV Infection," filed Aug. 1, 2013 (9 pages).
Office Action dated Feb. 23, 2017 for Chinese Application No. 201380051662.5, Shin et al., "Composition for Treating Cancer Associated with HPV Infection," filed Aug. 1, 2013 (11 pages).
Yamato et al., "New highly potent and specific E6 and E7 siRNAs for treatment of HPV16 positive cervical cancer," Cancer Gene Ther. 15(3):140-53 (2008).
International Search Report for International Application No. PCT/KR2013/006963, dated Nov. 27, 2013 (3 pages).
Office Action dated Nov. 7, 2017 for Japanese Application No. 2016-086754, Shin et al., "Composition for Treating Cancer Associated with HPV Infection," filed Apr. 25, 2016 (8 pages).
Corey, "Chemical modification: the key to clinical application of RNA interference?" J Clin Invest. 117(12):3615-22 (2007).
Office Action dated Feb. 20, 2018 for Russian Application No. 2017117878, Shin et al., "Composition for Treatment of Cancer Associated with HPV Infection," filed Apr. 25, 2016 (18 pages).
Office Action dated Feb. 8, 2018 for Canadian Application No. 2,880,777, Shin et al., "Composition for Treating Cancer Associated with HPV Infection," filed Apr. 25, 2016 (7 pages).
Prakash et al., "Positional effect of chemical modifications on short interference RNA activity in mammalian cells," J Med Chem. 48(13):4247-53 (2005).

\* cited by examiner

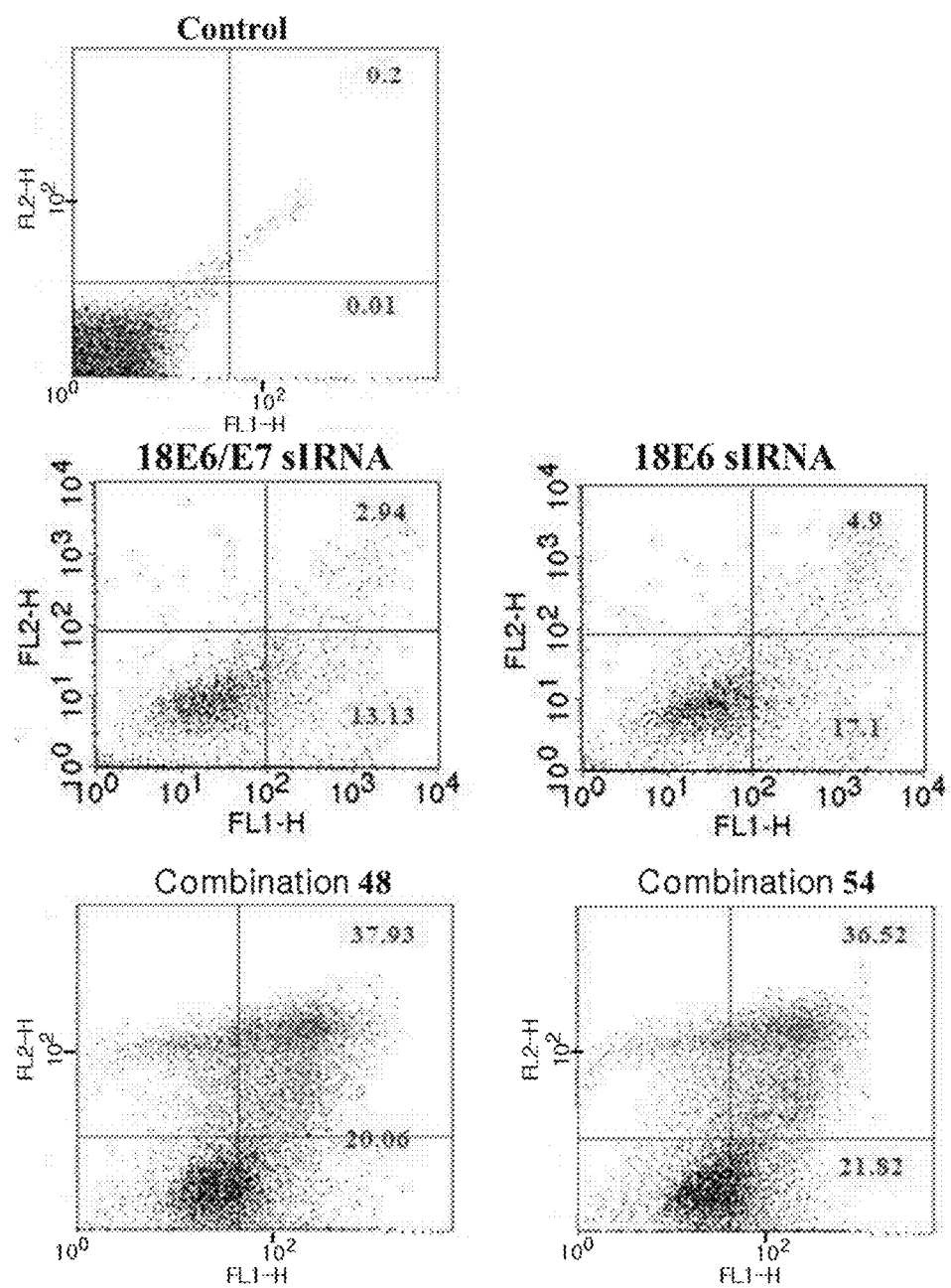

C : Control
1 : Combination2 (20nM)+CDDP
2 : Combination9 (20nM)+CDDP
3 : Combination13 (20nM)+CDDP
4 : CDDP
5 : Combination2 (10nM) + Combination9 (10nM)+CDDP
6 : Combination2 (10nM) + Combination13 (10nM)+CDDP
7 : Combination9 (10nM) + Combination13 (10nM)+CDDP
8 : Combination2 (7nM)+ Combination9 (7nM)+ Combination13 (7nM)+CDDP

IL-6

INF-gamma

Body Weight

Day 9

Day 28

1 : GFP siRNA + PBS
2 : CDDP + PTX
3 : CDDP + PTX + Combination 44 + Combination 51
4 : CDDP + PTX + Combination 48 + Combination 54

SEQUENCE LISTING

```
<160> NUMBER OF SEQ ID NOS: 113

<210> SEQ ID NO 1
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 1
gcaaagacau cuggacaaa                                                19

<210> SEQ ID NO 2
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (12)..(12)
<223> OTHER INFORMATION: n denotes o methyl modified uracil
<220> FEATURE:
<221> NAME/KEY: misc_feature
<222> LOCATION: (13)..(14)
<223> OTHER INFORMATION: n denotes o methyl modified guanine

<400> SEQUENCE: 2
gcaaagacau cnnnacaaa                                                19

<210> SEQ ID NO 3
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes o methyl modified guanine
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (13)..(14)
<223> OTHER INFORMATION: n denotes o methyl modified guanine

<400> SEQUENCE: 3
ncaaanacau cunnacaaa                                                19

<210> SEQ ID NO 4
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 4
uuuguccaga ugucuuugc                                                19

<210> SEQ ID NO 5
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: n denotes o methyl modified guanine
<220> FEATURE:
<221> NAME/KEY: misc_feature
<222> LOCATION: (9)..(9)
<223> OTHER INFORMATION: n denotes o methyl modified guanine
<220> FEATURE:
<221> NAME/KEY: misc_feature
<222> LOCATION: (12)..(12)
```

```
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine

<400> SEQUENCE: 5
uuunuccana unucuuunc                                              19

<210> SEQ ID NO 6
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (4)..(4)
<223> OTHER INFORMATION: n denotes o methyl modified guanine
<220> FEATURE:
<221> NAME/KEY: misc_feature
<222> LOCATION: (12)..(12)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified uracil

<400> SEQUENCE: 6 ununccaga unucunugc                                               19

<210> SEQ ID NO 7
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 7
ucaagaacac guagagaaa                                              19

<210> SEQ ID NO 8
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine

<400> SEQUENCE: 8
ucaanaacac nuananaaa                                              19
```

```
<210> SEQ ID NO 9
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 9
uuucucuacg uguucuuga                                              19

<210> SEQ ID NO 10
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(10)
<223> OTHER INFORMATION: n denotes o methyl modified guanine
<220> FEATURE:
<221> NAME/KEY: misc_feature
<222> LOCATION: (12)..(12)
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine

<400> SEQUENCE: 10
uuucucuacn unuucuuna                                              19

<210> SEQ ID NO 11
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified uracil
<220> FEATURE:
<221> NAME/KEY: misc_feature
<222> LOCATION: (13)..(13)
<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil

<400> SEQUENCE: 11
unucucuacg ngnucunga                                              19

<210> SEQ ID NO 12
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 12
gaccggucga uguaugucuu g                                           21

<210> SEQ ID NO 13
<211> LENGTH: 21
<212> TYPE: RNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (7)..(7)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified uracil
<220> FEATURE:
<221> NAME/KEY: misc_feature
<222> LOCATION: (13)..(13)
<223> OTHER INFORMATION: n denotes o methyl modified uracil
<220> FEATURE:
<221> NAME/KEY: misc_feature
<222> LOCATION: (15)..(15)
<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil
<220> FEATURE:
<221> NAME/KEY: misc_feature
<222> LOCATION: (19)..(19)
<223> OTHER INFORMATION: n denotes o methyl modified uracil

<400> SEQUENCE: 13
gaccggncga ngnangncnu g                                           21

<210> SEQ ID NO 14
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 14
agacauacau cgaccggucc a                                           21

<210> SEQ ID NO 15
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified uracil
<220> FEATURE:
<221> NAME/KEY: misc_feature
<222> LOCATION: (10)..(10)
<223> OTHER INFORMATION: n denotes o methyl modified uracil
<220> FEATURE:
<221> NAME/KEY: misc_feature
<222> LOCATION: (18)..(18)
<223> OTHER INFORMATION: n denotes o methyl modified uracil

<400> SEQUENCE: 15
agacanacan cgaccggncc a                                           21

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 16
ggagcgaccc agaaagtta                                              19
```

<210> SEQ ID NO 17
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified guanine
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (12)..(12)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine

<400> SEQUENCE: 17
gnagcnaccc anaaantta                                            19

<210> SEQ ID NO 18
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes F modified cytosine
<220> FEATURE:
<221> NAME/KEY: misc_feature
<222> LOCATION: (8)..(10)
<223> OTHER INFORMATION: n denotes F modified cytosine

<400> SEQUENCE: 18
ggagngannn agaaagtta                                            19

<210> SEQ ID NO 19
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 19
uaacuuucug ggucgcucc                                            19

<210> SEQ ID NO 20
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (9)..(9)
<223> OTHER INFORMATION: n denotes o methyl modified uracil
<220> FEATURE:
<221> NAME/KEY: misc_feature
<222> LOCATION: (13)..(13)

<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil

<400> SEQUENCE: 20
uaacnuucng ggncgcncc                                           19

<210> SEQ ID NO 21
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(11)
<223> OTHER INFORMATION: n denotes o methyl modified guanine
<220> FEATURE:
<221> NAME/KEY: misc_feature
<222> LOCATION: (15)..(15)
<223> OTHER INFORMATION: n denotes o methyl modified guanine

<400> SEQUENCE: 21
uaacuuucun ngucncucc                                           19

<210> SEQ ID NO 22
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 22
cagaaagtta ccacagtta                                           19

<210> SEQ ID NO 23
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified guanine
<220> FEATURE:
<221> NAME/KEY: misc_feature
<222> LOCATION: (7)..(7)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine

<400> SEQUENCE: 23
canaaantta ccacantta                                           19

<210> SEQ ID NO 24
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes F modified cytosine
<220> FEATURE:
<221> NAME/KEY: misc_feature
<222> LOCATION: (11)..(12)
<223> OTHER INFORMATION: n denotes F modified cytosine
<220> FEATURE:
<221> NAME/KEY: misc_feature
<222> LOCATION: (14)..(14)
<223> OTHER INFORMATION: n denotes F modified cytosine

<400> SEQUENCE: 24
nagaaagtta nnanagtta                                              19

<210> SEQ ID NO 25
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 25
uaacuguggu aacuuucug                                              19

<210> SEQ ID NO 26
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (10)..(10)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil
<220> FEATURE:
<221> NAME/KEY: misc_feature
<222> LOCATION: (18)..(18)
<223> OTHER INFORMATION: n denotes o methyl modified uracil

<400> SEQUENCE: 26
uaacnguggn aacnuucng                                              19

<210> SEQ ID NO 27
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (8)..(9)
<223> OTHER INFORMATION: n denotes o methyl modified guanine
<220> FEATURE:
<221> NAME/KEY: misc_feature
<222> LOCATION: (19)..(19)
<223> OTHER INFORMATION: n denotes o methyl modified guanine

<400> SEQUENCE: 27 uaacunnnu aacuuucun                                               19

<210> SEQ ID NO 28
<211> LENGTH: 19
<212> TYPE: DNA

<213> ORGANISM: Artificial Sequence
<220> FEATURE:
<223> OTHER INFORMATION: synthetic oligonucleotide

<400> SEQUENCE: 28
gcacagagct gcaaacaac                                              19

<210> SEQ ID NO 29
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes o methyl modified guanine
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine

<400> SEQUENCE: 29
ncacananct ncaaacaac                                              19

<210> SEQ ID NO 30
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes F modified cytosine
<220> FEATURE:
<221> NAME/KEY: misc_feature
<222> LOCATION: (9)..(9)
<223> OTHER INFORMATION: n denotes F modified cytosine
<220> FEATURE:
<221> NAME/KEY: misc_feature
<222> LOCATION: (12)..(12)
<223> OTHER INFORMATION: n denotes F modified cytosine
<220> FEATURE:
<221> NAME/KEY: misc_feature
<222> LOCATION: (16)..(16)
<223> OTHER INFORMATION: n denotes F modified cytosine

<400> SEQUENCE: 30
gnacagagnt gnaaanaac                                              19

<210> SEQ ID NO 31
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 31
guuguuugca gcucugugc                                              19

<210> SEQ ID NO 32
<211> LENGTH: 19

```
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (6)..(6)
<223> OTHER INFORMATION: n denotes o methyl modified uracil
<220> FEATURE:
<221> NAME/KEY: misc_feature
<222> LOCATION: (13)..(13)
<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil

<400> SEQUENCE: 32
gnugunugca gcncugngc                                                19

<210> SEQ ID NO 33
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine

<400> SEQUENCE: 33
guunuuunca ncucunugc                                                19

<210> SEQ ID NO 34
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 34
gcaaacaact atacatgat                                                19

<210> SEQ ID NO 35
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes o methyl modified guanine
<220> FEATURE:
<221> NAME/KEY: misc_feature
<222> LOCATION: (17)..(17)
```

<223> OTHER INFORMATION: n denotes o methyl modified guanine

<400> SEQUENCE: 35
ncaaacaact atacatnat                                              19

<210> SEQ ID NO 36
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes F modified cytosine
<220> FEATURE:
<221> NAME/KEY: misc_feature
<222> LOCATION: (6)..(6)
<223> OTHER INFORMATION: n denotes F modified cytosine
<220> FEATURE:
<221> NAME/KEY: misc_feature
<222> LOCATION: (9)..(9)
<223> OTHER INFORMATION: n denotes F modified cytosine
<220> FEATURE:
<221> NAME/KEY: misc_feature
<222> LOCATION: (14)..(14)
<223> OTHER INFORMATION: n denotes F modified cytosine

<400> SEQUENCE: 36
gnaaanaant atanatgat                                              19

<210> SEQ ID NO 37
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 37
aucauguaua guuguuugc                                              19

<210> SEQ ID NO 38
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (7)..(7)
<223> OTHER INFORMATION: n denotes o methyl modified uracil
<220> FEATURE:
<221> NAME/KEY: misc_feature
<222> LOCATION: (15)..(15)
<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil

<400> SEQUENCE: 38
ancaugnaua guugnungc                                              19

<210> SEQ ID NO 39
<211> LENGTH: 19
<212> TYPE: RNA
<213> ORGANISM: Artificial Sequence

```
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine

<400> SEQUENCE: 39
aucaunuaua nuunuuunc                                            19

<210> SEQ ID NO 40
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 40
agcaaagaca tctggacaa                                            19

<210> SEQ ID NO 41
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified guanine
<220> FEATURE:
<221> NAME/KEY: misc_feature
<222> LOCATION: (7)..(7)
<223> OTHER INFORMATION: n denotes o methyl modified guanine
<220> FEATURE:
<221> NAME/KEY: misc_feature
<222> LOCATION: (14)..(15)
<223> OTHER INFORMATION: n denotes o methyl modified guanine

<400> SEQUENCE: 41
ancaaanaca tctnnacaa                                            19

<210> SEQ ID NO 42
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes F modified cytosine
<220> FEATURE:
<221> NAME/KEY: misc_feature
<222> LOCATION: (9)..(9)
<223> OTHER INFORMATION: n denotes F modified cytosine
<220> FEATURE:
<221> NAME/KEY: misc_feature
<222> LOCATION: (12)..(12)
<223> OTHER INFORMATION: n denotes F modified cytosine
<220> FEATURE:
```

<221> NAME/KEY: misc_feature
<222> LOCATION: (17)..(17)
<223> OTHER INFORMATION: n denotes F modified cytosine

<400> SEQUENCE: 42
agnaaagana tntgganaa                                              19

<210> SEQ ID NO 43
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 43
uuguccagau gucuuugcu                                              19

<210> SEQ ID NO 44
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (12)..(12)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil
<220> FEATURE:
<221> NAME/KEY: misc_feature
<222> LOCATION: (16)..(16)
<223> OTHER INFORMATION: n denotes o methyl modified uracil

<400> SEQUENCE: 44
unguccagau gncnungcu                                              19

<210> SEQ ID NO 45
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (17)..(17)
<223> OTHER INFORMATION: n denotes o methyl modified guanine

<400> SEQUENCE: 45
uunuccanau nucuuuncu                                              19

<210> SEQ ID NO 46
<211> LENGTH: 21

```
<212> TYPE: RNA
<213> ORGANISM: Artificial Sequence
<220> FEATURE:
<223> OTHER INFORMATION: synthetic oligonucleotide

<400> SEQUENCE: 46
caccuacauu gcaugaauau a                                          21

<210> SEQ ID NO 47
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified uracil
<220> FEATURE:
<221> NAME/KEY: misc_feature
<222> LOCATION: (20)..(20)
<223> OTHER INFORMATION: n denotes o methyl modified uracil

<400> SEQUENCE: 47
caccnacauu ncangaauan a                                          21

<210> SEQ ID NO 48
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 48
uauauucaug caauguaggu g                                          21

<210> SEQ ID NO 49
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified uracil
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil
<220> FEATURE:
<221> NAME/KEY: misc_feature
<222> LOCATION: (20)..(20)
<223> OTHER INFORMATION: n denotes o methyl modified uracil

<400> SEQUENCE: 49
uananucaug caanguaggn g                                          21

<210> SEQ ID NO 50
```

```
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(10)
<223> OTHER INFORMATION: n denotes o methyl modified guanine
<220> FEATURE:
<221> NAME/KEY: misc_feature
<222> LOCATION: (15)..(15)
<223> OTHER INFORMATION: n denotes o methyl modified guanine
<220> FEATURE:
<221> NAME/KEY: misc_feature
<222> LOCATION: (18)..(19)
<223> OTHER INFORMATION: n denotes o methyl modified guanine

<400> SEQUENCE: 50
uauauucaun caaunuannu g                                        21

<210> SEQ ID NO 51
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 51
cuucgguugu gcguacaaag c                                        21

<210> SEQ ID NO 52
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (5)..(5)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified uracil

<400> SEQUENCE: 52
cnucnguugu ncgnacaaag c                                        21

<210> SEQ ID NO 53
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 53
gcuuuguacg cacaaccgaa g                                        21

<210> SEQ ID NO 54
<211> LENGTH: 21
<212> TYPE: RNA
<213> ORGANISM: Artificial Sequence
```

```
<220> FEATURE:
<223> OTHER INFORMATION: synthetic oligonucleotide
<220> FEATURE:
<221> NAME/KEY: misc_feature
<222> LOCATION: (3)..(5)
<223> OTHER INFORMATION: n denotes o methyl modified uracil
<220> FEATURE:
<221> NAME/KEY: misc_feature
<222> LOCATION: (7)..(7)
<223> OTHER INFORMATION: n denotes o methyl modified uracil

<400> SEQUENCE: 54
gcnnngnacg cacaaccgaa g                                              21

<210> SEQ ID NO 55
<211> LENGTH: 21
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (10)..(10)
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine
<220> FEATURE:
<221> NAME/KEY: misc_feature
<222> LOCATION: (21)..(21)
<223> OTHER INFORMATION: n denotes o methyl modified guanine

<400> SEQUENCE: 55
gcuuunuacn cacaaccnaa n                                              21

<210> SEQ ID NO 56
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 56
caaccgagca cgacaggaa                                                 19

<210> SEQ ID NO 57
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes F modified cytosine
<220> FEATURE:
<221> NAME/KEY: misc_feature
<222> LOCATION: (4)..(5)
<223> OTHER INFORMATION: n denotes F modified cytosine
<220> FEATURE:
<221> NAME/KEY: misc_feature
<222> LOCATION: (9)..(9)
<223> OTHER INFORMATION: n denotes F modified cytosine
<220> FEATURE:
<221> NAME/KEY: misc_feature
<222> LOCATION: (11)..(11)
<223> OTHER INFORMATION: n denotes F modified cytosine
<220> FEATURE:
```

```
<221> NAME/KEY: misc_feature
<222> LOCATION: (14)..(14)
<223> OTHER INFORMATION: n denotes F modified cytosine

<400> SEQUENCE: 57
naanngagna nganaggaa                                                  19

<210> SEQ ID NO 58
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (12)..(12)
<223> OTHER INFORMATION: n denotes o methyl modified guanine
<220> FEATURE:
<221> NAME/KEY: misc_feature
<222> LOCATION: (16)..(17)
<223> OTHER INFORMATION: n denotes o methyl modified guanine

<400> SEQUENCE: 58
caaccnanca cnacannaa                                                  19

<210> SEQ ID NO 59
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 59
uuccugucgu gcucgguug                                                  19

<210> SEQ ID NO 60
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (7)..(7)
<223> OTHER INFORMATION: n denotes o methyl modified uracil
<220> FEATURE:
<221> NAME/KEY: misc_feature
<222> LOCATION: (10)..(10)
<223> OTHER INFORMATION: n denotes o methyl modified uracil
<220> FEATURE:
<221> NAME/KEY: misc_feature
<222> LOCATION: (13)..(13)
<223> OTHER INFORMATION: n denotes o methyl modified uracil

<400> SEQUENCE: 60
uuccngncgn gcncgguug                                                  19

<210> SEQ ID NO 61
<211> LENGTH: 19
```

```
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(2)
<223> OTHER INFORMATION: n denotes o methyl modified uracil
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (7)..(7)
<223> OTHER INFORMATION: n denotes o methyl modified uracil
<220> FEATURE:
<221> NAME/KEY: misc_feature
<222> LOCATION: (10)..(10)
<223> OTHER INFORMATION: n denotes o methyl modified uracil
<220> FEATURE:
<221> NAME/KEY: misc_feature
<222> LOCATION: (13)..(13)
<223> OTHER INFORMATION: n denotes o methyl modified uracil

<400> SEQUENCE: 61
nnccngncgn gncgguug                                                   19

<210> SEQ ID NO 62
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 62
ccaacgacgc agagaaaca                                                  19

<210> SEQ ID NO 63
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (9)..(9)
<223> OTHER INFORMATION: n denotes o methyl modified guanine
<220> FEATURE:
<221> NAME/KEY: misc_feature
<222> LOCATION: (12)..(12)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine

<400> SEQUENCE: 63
ccaacnacnc ananaaaca                                                  19

<210> SEQ ID NO 64
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 64
```

```
uguuucucug cgucguugg                                              19

<210> SEQ ID NO 65
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: n denotes o methyl modified uracil
<220> FEATURE:
<221> NAME/KEY: misc_feature
<222> LOCATION: (9)..(9)
<223> OTHER INFORMATION: n denotes o methyl modified uracil
<220> FEATURE:
<221> NAME/KEY: misc_feature
<222> LOCATION: (13)..(13)
<223> OTHER INFORMATION: n denotes o methyl modified uracil
<220> FEATURE:
<221> NAME/KEY: misc_feature
<222> LOCATION: (16)..(16)
<223> OTHER INFORMATION: n denotes o methyl modified uracil

<400> SEQUENCE: 65
ugunucucng cgncgnugg                                              19

<210> SEQ ID NO 66
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 66
actgcaagac atagaaata                                              19

<210> SEQ ID NO 67
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (4)..(4)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine

<400> SEQUENCE: 67
actncaanac atanaaata                                              19

<210> SEQ ID NO 68
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes F modified cytosine
<220> FEATURE:
<221> NAME/KEY: misc_feature
```

```
<222> LOCATION: (5)..(5)
<223> OTHER INFORMATION: n denotes F modified cytosine
<220> FEATURE:
<221> NAME/KEY: misc_feature
<222> LOCATION: (10)..(10)
<223> OTHER INFORMATION: n denotes F modified cytosine

<400> SEQUENCE: 68
antgnaagan atagaaata                                              19

<210> SEQ ID NO 69
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 69
uauuucuaug ucuugcagu                                              19

<210> SEQ ID NO 70
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified uracil
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil

<400> SEQUENCE: 70
uanuncuaug ncungcagu                                              19

<210> SEQ ID NO 71
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (10)..(10)
<223> OTHER INFORMATION: n denotes o methyl modified guanine
<220> FEATURE:
<221> NAME/KEY: misc_feature
<222> LOCATION: (15)..(15)
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine

<400> SEQUENCE: 71
uauuucuaun ucuuncanu                                              19

<210> SEQ ID NO 72
<211> LENGTH: 19
<212> TYPE: DNA
```

```
<213> ORGANISM: Artificial Sequence
<220> FEATURE:
<223> OTHER INFORMATION: synthetic oligonucleotide

<400> SEQUENCE: 72
gtatattgca agacagtat                                                19

<210> SEQ ID NO 73
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (12)..(12)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine

<400> SEQUENCE: 73
ntatattnca anacantat                                                19

<210> SEQ ID NO 74
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (9)..(9)
<223> OTHER INFORMATION: n denotes F modified cytosine
<220> FEATURE:
<221> NAME/KEY: misc_feature
<222> LOCATION: (14)..(14)
<223> OTHER INFORMATION: n denotes F modified cytosine

<400> SEQUENCE: 74
gtatattgna aganagtat                                                19

<210> SEQ ID NO 75
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 75
auacugucuu gcaauauac                                                19

<210> SEQ ID NO 76
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
```

```
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (15)..(15)
<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil

<400> SEQUENCE: 76
anacngucuu gcaananac                                                19

<210> SEQ ID NO 77
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine

<400> SEQUENCE: 77
auacunucuu ncaauauac                                                19

<210> SEQ ID NO 78
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 78
gcaagacagt attggaact                                                19

<210> SEQ ID NO 79
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified guanine
<220> FEATURE:
<221> NAME/KEY: misc_feature
<222> LOCATION: (9)..(9)
<223> OTHER INFORMATION: n denotes o methyl modified guanine
<220> FEATURE:
<221> NAME/KEY: misc_feature
<222> LOCATION: (14)..(15)
<223> OTHER INFORMATION: n denotes o methyl modified guanine

<400> SEQUENCE: 79
gcaanacant attnnaact                                                19

<210> SEQ ID NO 80
<211> LENGTH: 19
<212> TYPE: DNA
<213> ORGANISM: Artificial Sequence
<220> FEATURE:
```

```
<223> OTHER INFORMATION: synthetic oligonucleotide
<220> FEATURE:
<221> NAME/KEY: misc_feature
<222> LOCATION: (2)..(2)
<223> OTHER INFORMATION: n denotes F modified cytosine
<220> FEATURE:
<221> NAME/KEY: misc_feature
<222> LOCATION: (7)..(7)
<223> OTHER INFORMATION: n denotes F modified cytosine
<220> FEATURE:
<221> NAME/KEY: misc_feature
<222> LOCATION: (18)..(18)
<223> OTHER INFORMATION: n denotes F modified cytosine

<400> SEQUENCE: 80
gnaaganagt attggaant                                                19

<210> SEQ ID NO 81
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 81
aguuccaaua cugucuugc                                                19

<210> SEQ ID NO 82
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified uracil
<220> FEATURE:
<221> NAME/KEY: misc_feature
<222> LOCATION: (9)..(9)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil

<400> SEQUENCE: 82
agnuccaana cugncuugc                                                19

<210> SEQ ID NO 83
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified guanine
<220> FEATURE:
<221> NAME/KEY: misc_feature
<222> LOCATION: (9)..(9)
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine

<400> SEQUENCE: 83
anuuccaana cugucuunc                                                19
```

```
<210> SEQ ID NO 84
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 84
attggaactt acagaggta                                               19

<210> SEQ ID NO 85
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine
<220> FEATURE:
<221> NAME/KEY: misc_feature
<222> LOCATION: (16)..(17)
<223> OTHER INFORMATION: n denotes o methyl modified guanine

<400> SEQUENCE: 85
attgnaactt acanannta                                               19

<210> SEQ ID NO 86
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n denotes F modified cytosine
<220> FEATURE:
<221> NAME/KEY: misc_feature
<222> LOCATION: (12)..(12)
<223> OTHER INFORMATION: n denotes F modified cytosine

<400> SEQUENCE: 86
attggaantt anagaggta                                               19

<210> SEQ ID NO 87
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 87
uaccucugua aguuccaau                                               19

<210> SEQ ID NO 88
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified uracil
<220> FEATURE:
```

<221> NAME/KEY: misc_feature
<222> LOCATION: (7)..(7)
<223> OTHER INFORMATION: n denotes o methyl modified uracil
<220> FEATURE:
<221> NAME/KEY: misc_feature
<222> LOCATION: (13)..(14)
<223> OTHER INFORMATION: n denotes o methyl modified uracil

<400> SEQUENCE: 88
uaccncngua agnnccaau                                              19

<210> SEQ ID NO 89
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n denotes o methyl modified uracil
<220> FEATURE:
<221> NAME/KEY: misc_feature
<222> LOCATION: (12)..(12)
<223> OTHER INFORMATION: n denotes o methyl modified uracil

<400> SEQUENCE: 89
uaccucunua anuuccaau                                              19

<210> SEQ ID NO 90
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 90
ctccaacgac gcagagaaa                                              19

<210> SEQ ID NO 91
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine

<400> SEQUENCE: 91
ctccaacnac ncananaaa                                              19

<210> SEQ ID NO 92
<211> LENGTH: 19
<212> TYPE: DNA
<213> ORGANISM: Artificial Sequence
<220> FEATURE:
<223> OTHER INFORMATION: synthetic oligonucleotide

```
<220> FEATURE:
<221> NAME/KEY: misc_feature
<222> LOCATION: (3)..(3)
<223> OTHER INFORMATION: n denotes F modified cytosine
<220> FEATURE:
<221> NAME/KEY: misc_feature
<222> LOCATION: (7)..(7)
<223> OTHER INFORMATION: n denotes F modified cytosine
<220> FEATURE:
<221> NAME/KEY: misc_feature
<222> LOCATION: (10)..(10)
<223> OTHER INFORMATION: n denotes F modified cytosine
<220> FEATURE:
<221> NAME/KEY: misc_feature
<222> LOCATION: (12)..(12)
<223> OTHER INFORMATION: n denotes F modified cytosine

<400> SEQUENCE: 92
ctncaangan gnagagaaa                                               19

<210> SEQ ID NO 93
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 93
uuucucugcg ucguuggag                                               19

<210> SEQ ID NO 94
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil

<400> SEQUENCE: 94
unucncugcg ncgnuggag                                               19

<210> SEQ ID NO 95
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (10)..(10)
<223> OTHER INFORMATION: n denotes o methyl modified guanine
<220> FEATURE:
<221> NAME/KEY: misc_feature
<222> LOCATION: (13)..(13)
```

<223> OTHER INFORMATION: n denotes o methyl modified guanine
<220> FEATURE:
<221> NAME/KEY: misc_feature
<222> LOCATION: (17)..(17)
<223> OTHER INFORMATION: n denotes o methyl modified guanine

<400> SEQUENCE: 95
uuucucuncn ucnuugnag                                           19

<210> SEQ ID NO 96
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 96
acgcagagaa acacaagta                                           19

<210> SEQ ID NO 97
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified guanine
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (17)..(17)
<223> OTHER INFORMATION: n denotes o methyl modified guanine

<400> SEQUENCE: 97
acncananaa acacaanta                                           19

<210> SEQ ID NO 98
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes F modified cytosine
<220> FEATURE:
<221> NAME/KEY: misc_feature
<222> LOCATION: (4)..(4)
<223> OTHER INFORMATION: n denotes F modified cytosine
<220> FEATURE:
<221> NAME/KEY: misc_feature
<222> LOCATION: (12)..(12)
<223> OTHER INFORMATION: n denotes F modified cytosine
<220> FEATURE:
<221> NAME/KEY: misc_feature
<222> LOCATION: (14)..(14)
<223> OTHER INFORMATION: n denotes F modified cytosine

<400> SEQUENCE: 98
angnagagaa ananaagta                                           19

```
<210> SEQ ID NO 99
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 99
uacuuguguu ucucugcgu                                                  19

<210> SEQ ID NO 100
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (5)..(5)
<223> OTHER INFORMATION: n denotes o methyl modified uracil
<220> FEATURE:
<221> NAME/KEY: misc_feature
<222> LOCATION: (7)..(7)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified uracil
<220> FEATURE:
<221> NAME/KEY: misc_feature
<222> LOCATION: (15)..(15)
<223> OTHER INFORMATION: n denotes o methyl modified uracil

<400> SEQUENCE: 100
uacungnguu ncucngcgu                                                  19

<210> SEQ ID NO 101
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (8)..(8)
<223> OTHER INFORMATION: n denotes o methyl modified guanine
<220> FEATURE:
<221> NAME/KEY: misc_feature
<222> LOCATION: (16)..(16)
<223> OTHER INFORMATION: n denotes o methyl modified guanine
<220> FEATURE:
<221> NAME/KEY: misc_feature
<222> LOCATION: (18)..(18)
<223> OTHER INFORMATION: n denotes o methyl modified guanine

<400> SEQUENCE: 101
uacuununuu ucucuncnu                                                  19

<210> SEQ ID NO 102
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 102
gcagagaaac acaagtata                                                  19
```

```
<210> SEQ ID NO 103
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n denotes o methyl modified guanine
<220> FEATURE:
<221> NAME/KEY: misc_feature
<222> LOCATION: (4)..(4)
<223> OTHER INFORMATION: n denotes o methyl modified guanine
<220> FEATURE:
<221> NAME/KEY: misc_feature
<222> LOCATION: (6)..(6)
<223> OTHER INFORMATION: n denotes o methyl modified guanine
<220> FEATURE:
<221> NAME/KEY: misc_feature
<222> LOCATION: (15)..(15)
<223> OTHER INFORMATION: n denotes o methyl modified guanine

<400> SEQUENCE: 103
ncananaaac acaantata                                            19

<210> SEQ ID NO 104
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes F modified cytosine
<220> FEATURE:
<221> NAME/KEY: misc_feature
<222> LOCATION: (10)..(10)
<223> OTHER INFORMATION: n denotes F modified cytosine
<220> FEATURE:
<221> NAME/KEY: misc_feature
<222> LOCATION: (12)..(12)
<223> OTHER INFORMATION: n denotes F modified cytosine

<400> SEQUENCE: 104
gnagagaaan anaagtata                                            19

<210> SEQ ID NO 105
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 105
uauacuugug uuucucugc                                            19

<210> SEQ ID NO 106
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified uracil
<220> FEATURE:
<221> NAME/KEY: misc_feature
<222> LOCATION: (11)..(11)
<223> OTHER INFORMATION: n denotes o methyl modified uracil
```

-continued

```
<220> FEATURE:
<221> NAME/KEY: misc_feature
<222> LOCATION: (15)..(15)
<223> OTHER INFORMATION: n denotes o methyl modified uracil
<220> FEATURE:
<221> NAME/KEY: misc_feature
<222> LOCATION: (17)..(17)
<223> OTHER INFORMATION: n denotes o methyl modified uracil

<400> SEQUENCE: 106
uanacuugug nuucncngc                                                19

<210> SEQ ID NO 107
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)..(8)
<223> OTHER INFORMATION: n denotes o methyl modified uracil
<220> FEATURE:
<221> NAME/KEY: misc_feature
<222> LOCATION: (10)..(10)
<223> OTHER INFORMATION: n denotes o methyl modified uracil
<220> FEATURE:
<221> NAME/KEY: misc_feature
<222> LOCATION: (18)..(18)
<223> OTHER INFORMATION: n denotes o methyl modified uracil

<400> SEQUENCE: 107
uauacuunun uuucucunc                                                19

<210> SEQ ID NO 108
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 108
cagagaaaca caagtataa                                                19

<210> SEQ ID NO 109
<211> LENGTH: 19
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (3)..(3)
<223> OTHER INFORMATION: n denotes o methyl modified guanine
<220> FEATURE:
<221> NAME/KEY: misc_feature
<222> LOCATION: (5)..(5)
<223> OTHER INFORMATION: n denotes o methyl modified guanine
<220> FEATURE:
<221> NAME/KEY: misc_feature
<222> LOCATION: (14)..(14)
<223> OTHER INFORMATION: n denotes o methyl modified guanine

<400> SEQUENCE: 109
cananaaaca caantataa                                                19

<210> SEQ ID NO 110
<211> LENGTH: 19
<212> TYPE: DNA
<213> ORGANISM: Artificial Sequence
<220> FEATURE:
```

```
<223> OTHER INFORMATION: synthetic oligonucleotide
<220> FEATURE:
<221> NAME/KEY: misc_feature
<222> LOCATION: (1)..(1)
<223> OTHER INFORMATION: n denotes F modified cytosine
<220> FEATURE:
<221> NAME/KEY: misc_feature
<222> LOCATION: (9)..(9)
<223> OTHER INFORMATION: n denotes F modified cytosine
<220> FEATURE:
<221> NAME/KEY: misc_feature
<222> LOCATION: (11)..(11)
<223> OTHER INFORMATION: n denotes F modified cytosine

<400> SEQUENCE: 110
nagagaaana naagtataa                                              19

<210> SEQ ID NO 111
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 111
uuauacuugu guucucug                                               19

<210> SEQ ID NO 112
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n denotes o methyl modified uracil
<220> FEATURE:
<221> NAME/KEY: misc_feature
<222> LOCATION: (8)..(8)
<223> OTHER INFORMATION: n denotes o methyl modified uracil
<220> FEATURE:
<221> NAME/KEY: misc_feature
<222> LOCATION: (14)..(14)
<223> OTHER INFORMATION: n denotes o methyl modified uracil
<220> FEATURE:
<221> NAME/KEY: misc_feature
<222> LOCATION: (18)..(18)
<223> OTHER INFORMATION: n denotes o methyl modified uracil

<400> SEQUENCE: 112
unauacungu guuncucng                                              19

<210> SEQ ID NO 113
<211> LENGTH: 19
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (9)..(9)
<223> OTHER INFORMATION: n denotes o methyl modified guanine
<220> FEATURE:
<221> NAME/KEY: misc_feature
<222> LOCATION: (11)..(11)
<223> OTHER INFORMATION: n denotes o methyl modified guanine
```

```
-continued

<220> FEATURE:
<221> NAME/KEY: misc_feature
<222> LOCATION: (19)..(19)
<223> OTHER INFORMATION: n denotes o methyl modified guanine

<400> SEQUENCE: 113
uuauacuunu nuuucucun                                              19
```

COMPOSITION FOR TREATING CANCER ASSOCIATED WITH HPV INFECTION

TECHNICAL FIELD

This patent application claims priority of Korean Patent Application No. 10-2012-0084820, filed on Aug. 2, 2012, the entire content of which is hereby incorporated by reference.

The present invention relates to a composition for gene therapy for a disease associated with HPV infection including cervical cancer.

BACKGROUND ART

High-risk human papilloma virus (hereinafter, "HPV") types and 18 are major factors of cervical cancer and cervical dysplasia, and become causes of other genital cancers and a head and neck squamous cancer. Cervical cancer is one of the most general types of malignant tumors of women. Although the incidence of invasive cervical cancer has been slowly reduced, the invasive cervical cancer is a still most frequent cancer of women in developing countries, which holds 25% of female cancers. HPV is a small DNA virus having approximately 8,000 base sequences which causes benign or malignant tumors. So far, depending on a genomic difference, at least about 100 HPV subtypes have been identified, and genotypes of approximately HPVs have been completely analyzed. Among these types, high-risk HPV types (e.g., HPV-16, 18, 31, 33, 35, 45, 51, 52, and 56) relate to almost 90% of cervical cancer. At least 50% of cervical cancer infected with HPV relate to HPV type 16, and followed by HPV type 18 (12%), HPV type 45 (8%), and HPV type (5%). These HPVs encode 2 oncogenic proteins, which are, protein E6 and E7. Both proteins are involved in HPV-mediated cell immortalization and cell transformation. The oncogenic E6 protein binds to wild-type p53 tumor suppressor protein to thereby degrade p53 through an ubiquitin pathway. On the other hand, the E7 protein directly binds to Rb to thereby overphosphorylate Rb. At first, E6 forms a complex with an E6-associated protein (E6-AP) which is an E3 ubiquitin-protein ligase. Then, the E6/E6-AP complex binds to and ubiquitinate wild-type p53, and then interferes with p53-mediated cellular reaction to DNA damage. Mostly, the p53 tumor suppressor protein is regulated by Mdm2-mediated ubiquitination, however, in HPV-infected cervical cancer cells, degradation of p53 is completely changed to E6-mediated ubiquitination from Mdm2-mediated ubiquitination. Thus, unlike many other cancers, most cases of HPV-infected cervical cancer have the wild-type p53 gene. However, an expression level of the p53 protein is very low due to the consistent degradation by the E6 protein. Particularly, the HPV E6 protein has been significantly noticeable as a specific target for killing just cervical cancer cells. These strategies, targeting to E6 or the E6/E6-AP complex, include various treatment.

Examples include: use of a cellular toxin agent, an inhibitor to release zinc of the E6 oncogenic protein, an epitope peptide (mimotope) mimicking E6-AP, anti-E6 ribozyme, a peptide aptamer which is targeted to the E6 oncogenic protein of a virus, siRNA which is targeted to the E6 oncogenic protein of the virus, and a combined treatment thereof. Recently, it has been proven that siRNA selectively silences an intrinsic gene in animal cells, and as well as, selectively silences a viral gene in a disease caused by a virus. RNA interference (RNAi) due to transfection of siRNA has been emerged as a novel therapy for treating viral infection of the human. siRNA, which is targeted to E6 and E7 genes in HPV-infected cervical cancer cells, causes p53 and pRb accumulation which leads to apoptosis or cell senescence. For an HPV-16 infected cervical cancer cell line and an HPV-18 infected cell line, it has been found that RNAi, which is targeted to E6 and E7 oncogenes of viruses, selectively sciences expression of these proteins.

Meanwhile, efficacy of a nucleic acid having various modifications for nucleic acids (for example, in a base, a sugar and/or phosphate) is enhanced by inhibiting degradation caused by serum ribonuclease. Several examples describing sugar, base and phosphate modifications, which may be introduced to a nucleic acid, are known in the art. For example, an oligonucleotide is modified to enhance stability and/or enhance the biological activity through a modification by a nuclease-resistant group, for example, through 2'-amino, 2'-C-allyl, 2'-fluoro, 2'-O-methyl, and 2'-H nucleotide base modification (see Eckstein et al., PCT Laid-open Publication WO 92/07065; document [Perrault et al., Nature 344:565-568, 1990]; document [Pieken et al., Science 253: 314-317, 1991]; document [Usman and Cedergren, Trends in Biochem. Sci. 17: 334-339, 1992]; Usman et al. PCT Laid-open Publication WO 93/15187; Sproat, U.S. Pat. No. 5,334,711 and document [Beigelman et al., J. Biol. Chem., 270:25702, 1995]; Beigelman et al., PCT Laid-open Publication WO 97/26270; Beigelman et al., U.S. Pat. No. 5,716, 824; Usman et al., U.S. Pat. No. 5,627,053; Woolf et al., PCT Laid-open Publication WO 98/13526; Thompson et al., U.S. Patent Application No. 60/082,404 (filed on Apr. 20, 1998); document [Karpeisky et al., Tetrahedron Lett., 39:1131, 1998]; document [Earnshaw and Gait, Biopolymers (Nucleic acid Sciences) 48:39-55, 1998]; document [Verma and Eckstein, Annu. Rev. Biochem. 67:99-134, 1998]; and document [Burlina et al., Bioorg. Med. Chem. 5: 1999-2010, 1997]). Similar modifications may be used to modify the nucleic acid of the present invention.

In 1999, as a result of combined therapy of cisplatin-based chemotherapy and radiotherapy, survival rate of women who have a severe cervical cancer in local has been significantly improved. Currently, cisplatin is a DNA-damaging drug which is widely used to treat cancers including ovarian, cervical, head and neck, non-small cell lung cancers and so forth. More recently, a working mechanism of a medicine based on platinum has been investigated. However, it is still not fully understood about a process in cells including DNA repair, cell death, cell cycle trajectory, signaling of DNA damage, and regulation in absorption and secretion of a drug due to cisplatin treatment. In HPV-18 HeLa cells, the p53 protein is escaped from E6-mediated degradation and preferentially accumulated in nucleolus of a nucleus after cisplatin treatment. Also, HPV-16 SiHa cells recover p53 function by simultaneous radiotherapy and cisplatin treatment, thereby increasing radiosusceptibility.

Therefore, as a result of attempting to investigate an effective siRNA having a novel sequence by imparting a chemical modification to E6/E7-specific siRNA so that the siRNA may show the anti-cancer effect, alone or in a complex combination, or show a synergistic effect when performing combination therapy with conventional chemotherapy or radiotherapy, the present inventors have found that nucleotides listed on following Examples and Claims and particular combinations thereof reduce expression of relating proteins TP53 and E7, and HPV E6 mRNA, and induce cell death, and also experimentally proven that efficacy achieved when used alone or in combination with anti-cancer agents is much better than that of RNA, which does not have a base sequence residue modification.

Throughout the specification, numerous journals and patent documents are referenced, and the citation is indicated. Disclosures of cited journals and patent documents are incorporated herein in their entireties by reference to more clearly describe the level of the technical field to which the present invention belongs and features of the present invention.

DISCLOSURE OF THE INVENTION

Technical Problem

The present inventors continuously study and try to develop an efficient gene therapeutic agent for various diseases caused by human papilloma virus (HPV) infection. As a result, the present invention has been completed by finding that when using particular RNA for inhibiting expression, which is targeted to an E6/E7 gene of HPV type 16 or HPV type 18 virus, or a RNA sequence having a modification in a base of the RNA, HPV gene expression is efficiently inhibited, to thereby show an excellent therapeutic activity on diseases associated with HPV infection including a cervical cancer.

One object of the present invention is to provide a composition for preventing or treating a disease associated with HPV infection, more particularly, an HPV infection-associated cancer, and further more particularly a cervical cancer.

Another object of the present invention is to provide a method for preventing or treating a disease associated with HPV infection, more particularly, an HPV infection-associated cancer, and further more particularly a cervical cancer.

Other objects and benefits of the present invention become clear by appended detailed description of the invention, claims, and drawings.

Technical Solution

According to one aspect of the present invention, the present invention provides a composition for treating or preventing a disease associated with human papilloma virus (HPV) infection, the composition including, as an active ingredient, one or more nucleotide sequences selected from the group consisting of sequences of SEQ ID NOs: 16, 22, 28, 34, 40, 66, 72, 84, 90, and 108, and antisense nucleotide sequences thereof.

The present inventors continuously study and try to develop an efficient gene therapeutic agent for various diseases caused by HPV infection. Consequently, it has been found that when using particular RNA for inhibiting expression, which is targeted to E6/E7 genes of HPV type 16 or HPV type 18 virus, or a RNA sequence having a modification in a base of the RNA, HPV gene expression is efficiently inhibited to thereby show an excellent therapeutic activity on diseases associated with HPV infection including cervical cancer.

According to the present invention, sequences of SEQ ID Nos: 16, 22, 28, 34, and 40 and sequences of SEQ ID Nos: 72, 84 90, and 108 are RNA nucleic acid sequences for inhibiting expression, wherein sequences of SEQ ID Nos: 16, 22, 28, 34, and 40 are targeted to HPV type 16 virus; and sequences of SEQ ID Nos: 72, 84 90, and 108 are targeted to HPV type 16 virus.

As used herein, the term "nucleotide" means a ribonucleotide present in a single strand or a double strand form, and includes a natural nucleotide analogue unless otherwise specifically indicated (see Scheit, *Nucleotide Analogs*, John Wiley, New York (1980); Uhlman and Peyman, *Chemical Reviews*, 90:543-584(1990)).

As used herein, the term "inhibition of expression" means to lead decline in a function of a target gene, and preferably means that expression of the target gene become undetectable or resultantly exists at the meaningless level According to a preferred embodiment of the present invention, the nucleotide sequence of the present invention is an RNA sequence having an ability to silence E6/E7 genes of HPV type 18 or HPV type 16 virus, and preferably, siRNA, shRNA, or an antisense oligonucleotide.

As used herein, the term "siRNA" means short double chain RNA which may induce RNA interference (RNAi) through cleavage of particular mRNA. The siRNA consist of a sense RNA strand having a homologous sequence with mRNA of a target gene, and an antisense RNA strand having a complementary sequence thereto. siRNA can inhibit expression of the target gene, and is thus provided as an efficient gene knock-down method or a gene therapy method.

siRNA is not limited such that siRNA having a double chain RNA part with RNA pairs is completely paired; rather includes a part which does not form a pair because of mismatch (i.e., a corresponding base is not complementary), bulge (i.e., there is no base corresponding to one-side chain), and so forth. The total length is 10 to 100 bases, preferably 15 to 80 bases, and most preferably 17 to 23 bases. Both a blunt end and a cohesive end are available as an siRNA end structure, if it is possible to inhibit target gene expression by the RNAi effect. For the cohesive end structure, both a 3 end protrusion structure and a 5 end protrusion structure are available. The number of protruded bases is not limited. For example, the number of bases may become 1 to 8 bases, and preferably 2 to 6 bases. In addition, siRNA may include, for example, low-molecular weight RNA (e.g., natural RNA molecules such as tRNA, rRNA, and viral RNA, or synthetic RNA molecules) in a protrusion part of one end in the range where the effect of inhibiting target gene expression may be retained. In the end structure of siRNA, it is not necessary to have a cleavage structure in both sides, and the structure may be a stem-loop structure in which an end-portion of one side of double chain RNA is connected by linker RNA. A length of the linker is not particularly limited unless the length affects paring in a stem part.

As used herein, the term "small hairpin RNA (shRNA)" means 50 to 70 single-stranded nucleotides, and forms the stem-loop structure in vivo. In other word, shRNA is a RNA sequence to form a tight hairpin structure to inhibit gene expression through RNA interference. A double strand stem is formed by base-pairing of long RNA having 15 to 30 complementary nucleotides at both sides of a loop site having 5 to 10 nucleotides. For constitutive expression, shRNA is transduced into cells through a vector including U6 promoter, and mostly transferred to daughter cells to hereditary transmit inhibition of gene expression. The shRNA hairpin structure is cleaved by an intracellular mechanism to become siRNA, and then binds to an RNA-induced silencing complex (RISC). These RISCs bind to and cleave mRNA. shRNA is transcribed by RNA polymerase □. According to the present invention, the nucleotide sequence of the present invention may form the shRNA structure having a double strand stem sequence at both sides of the loop site.

As used herein, the term "microRNA (miRNA)" means a single strand RNA molecule which regulates gene expression and includes 10 to 50 nucleotides in full-length, preferably 15 to nucleotides, and more preferably 17 to 25 nucleotides. miRNA is an oligonucleotide which is not expressed in cells and has a short stem-loop structure. miRNA is fully or partially homologous with at least one messenger RNA (mRNA), and inhibits target gene expression by complementarily binding to the mRNA.

As used herein, the term "antisense oligonucleotide" means RNA containing a nucleotide sequence complementary to a particular mRNA sequence, or a derivative thereof, and inhibits translation of mRNA into a protein by binding to the complementary sequence in mRNA. The antisense nucleotide sequence of the present invention means an RNA sequence that may be complementary to mRNA of a target gene to bind to mRNA of the target gene, and may inhibit translation of the target gene into mRNA, translocation into cytoplasm, maturation, or other essential activities for overall biological functions.

To enhance efficacy of the antisense oligonucleotide, a modification may be made at a position of one or more of bases, sugars or backbones (see De Mesmaeker et al., *Curr Opin Struct Biol.*, 5(3):343-55, 1995). The oligonucleotide backbone may be modified with phosphorothioate, phosphotriester, methyl phosphonate, single-chain alkyl, cycloalkyl, single-chain heteroatomic, heterocyclic sugar sulfonate, and so forth. In addition, an antisense nucleic acid may include one or more substituted sugar moieties. The antisense oligonucleotide may include a modified base. Examples of modified bases include hypoxanthine, 6-methyl adenine, 5-methyl pyrimidine (particularly, 5-methyl cytosine), 5-hydroxymethyl cytosine (HMC), glycosyl HMC, gentobiosyl HMC, 2-aminoadenine, 2-tiouracil, 2-tiothymine, 5-bromouracil, 5-hydroxymethyl uracil, 8-azaguanin, 7-deazaguanin, N6(6-aminohexyl)adenine, 2,6-diaminopurine, 2-O-methyl uracil, 2-O-methylguanin, 2-fluorocytisine, and so forth.

According to a more preferred embodiment of the present invention, the nucleotide sequence of the present invention is an siRNA sequence.

According to another aspect of the present invention, the present invention provides a composition for treating or preventing a disease associated with HPV infection, the composition including, as an active ingredient, one or more nucleotide sequences selected from the group consisting of sequences of SEQ ID NOs: 1, 7, 12, 16, 22, 28, 34, 40, 46, 51, 56, 62, 66, 72, 78, 84, 90, 96, 102 and 108, and antisense nucleotide sequences thereof, which have a modified backbone or one or more modified bases. In other word, a nucleotide having the nucleotide sequences listed above, in which a backbone or a base is modified, may become the composition of the present invention for preventing or treating a disease associated with HPV infection.

Modifications of a backbone or a base to be applied to the nucleotide of the present invention may include any modification which is conventionally employed in the art to increase stability or the desired activity.

Preferably, the modified backbone of the present invention includes one or more modifications selected from the group consisting of alkylphosphonate, phosphorothioate, phosphorodithioate, alkylphosphonothioate, phosphoamidate, phosphate ester, carbamate, acetamidate, carboxymethyl ester, carbonate, and phosphate triester.

Preferably, the modified base of the present invention includes one or more modifications selected from the group consisting of methylation, glycosylation and halogenation. More preferably, the modified base of the present invention is a 2'-O methylated or a 2'-fluorinated base.

According to the present invention, when imparting a modification such as 2'-O methylation or 2'-fluorination to a particular position of RNA targeted to E6/E7 genes of HPV type or HPV type 18 virus for inhibiting expression, comparing with an unmodified nucleic acid molecule, the present inventors have found that: efficiency of inhibiting target gene expression is remarkably increased; stability in human serum is increased; and half-life is considerably increased by at least two times in a pharmacokinetic experiment in animals.

2'-O methylation means that a hydroxyl group attached to carbon number two of ribose of an RNA molecule is methylated, and thus modified to a 2'-methoxy group; and 2'-fluorination means that the hydroxyl group attached to carbon number two of ribose of the RNA molecule is substituted with a fluoro group and thus modified to a 2'-fluoro group.

According to a preferred embodiment of the present invention, the 2'-o methylated base in the nucleotide of the present invention is U or G.

According to a preferred embodiment of the present invention, the 2'-fluorinated base in the nucleotide of the present invention is C.

According to a preferred embodiment of the present invention, the nucleotide sequence of the present invention having one or more of the 2'-O methylated or the 2'-fluorinated base is selected from the group consisting of sequences of SEQ ID NOs: 2, 3, 5, 6, 8, 10, 11, 13, 15, 17, 18, 20, 21, 23, 24, 26, 27, 29, 30, 32, 33, 35, 36, 38, 39, 41, 42, 44, 45, 47, 49, 50, 52, 54, 55, 57, 58, 60, 61, 63, 65, 67, 68, 70, 71, 73, 74, 76, 77, 79, 80, 82, 83, 85, 86, 88, 89, 91, 92, 94, 95, 97, 98, 100, 101, 103, 104, 106, 107, 109, 110, 112 and 113.

According to another embodiment of the present invention, the present invention provides a composition for preventing or treating a disease associated with HPV infection, the composition including, as an active ingredient, a nucleotide pool selected from the group consisting of: a pool having nucleotide sequences of SEQ ID Nos: 2, 4, 8, 9, 12, and 15; a pool having nucleotide sequences of SEQ ID Nos: 18, 21, 29, and 32; a pool having nucleotide sequences of SEQ ID Nos: 42, 45, 52, and 55; a pool having nucleotide sequences of SEQ ID Nos: 58, 59, 63 and 65; a pool having nucleotide sequences of SEQ ID Nos: 68, 71, 91 and 94; and a pool having nucleotide sequences of SEQ ID Nos: 98, 100, 109 and 112.

According to the present invention, the present inventors have found that when the nucleotide sequence of the present invention is used as a pool having particular combination, efficiency of inhibiting target gene expression is considerably increased, when compared with the case where a single sequence of RNA is used, so that a more outstanding therapeutic activity to a disease associated with HPV infection is achieved.

According to a preferred embodiment of the present invention, a disease associated with HPV infection to be treated by the composition of the present invention is selected from the group consisting of genital warts, vagina inflammation, pelvic inflammation and a cancer, and more preferably, a cancer treated by the composition of the present invention is selected from the group consisting of cervical cancer, vagina cancer, vulva cancer, anal cancer, penis cancer, tonsil cancer, pharynx cancer, larynx cancer, head and neck cancer and lung adenocarcinoma. Most preferably, the cancer to be treated by the composition of the present invention is cervical cancer.

The composition of the present invention may be prepared as a pharmaceutical composition including a pharmaceutically effective amount of the nucleic acid molecule of the present invention.

As used herein, the term "pharmaceutically effective amount" means an amount sufficient to achieve the activity or efficacy of treating, alleviating, or preventing arthritis, as described above, of the present invention.

A pharmaceutically acceptable carrier, which is included in the pharmaceutical composition of the present invention, is one typically used in preparation, and includes, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, cyclodextrin and a copolymer thereof, mineral oil, and so forth. The pharmaceutical composition of the present invention may further include a lubricant, a humectant, a sweetening agent, a favoring agent, an emulsifier, a suspending agent, and a preserving agent besides the components above. A suitable pharmaceutically acceptable carrier and a preparation are described in Remington's Pharmaceutical Sciences (19th ed., 1995).

The pharmaceutical composition of the present invention may be orally or parenterally administered, and preferably parenterally administered. For parenteral administration, intravenous infusion, subcutaneous infusion, intramuscular infusion, peritoneal infusion, topical administration, transdermal administration, and intraarticular administration may be used.

Suitable administration dose of the pharmaceutical composition of the present invention may be differentially prescribed depending on various factors such as a method for formulation, a mode of administration, age, weight, sex, and disease states, dietary of patients, time of administration, a route of administration, a secretion rate and reaction susceptibility. A preferable administration dose of the pharmaceutical composition of the present invention is 0.0001 to 100 mg/kg per day.

When the pharmaceutical composition of the present invention is used as an anti-cancer agent, the composition may be used as combination with the anti-cancer composition typically used in the art. More specifically, the composition may be combinatorially administered with anti-cancer agents such as cisplatin or paclitaxel.

The pharmaceutical composition of the present invention is prepared in a unit dosage form by being formulated using a pharmaceutically acceptable carrier and/or excipient, or prepared by being incorporated into a multi-dose container, according to a method by which a person with ordinary skill in the technical field to which the present invention belongs could easily carry out. In this case, the formulation may be a form of a solution, suspension, or emulsion in an oil or an aqueous medium, or extract, powder, granule, tablet, or capsule form, and may further include a dispersing agent or a stabilizer.

According to more preferred embodiment of the present invention, the nucleic acid molecule of the present invention is included in a gene delivery system.

As used herein, the term "gene delivery system" means a mediator to introduce a desired target gene in subject cells to express. The ideal gene delivery system should be non-toxic to the human body, easily mass produced, and deliver efficiently the gene.

As used herein, the term "gene delivery" means delivering the gene into cells, and has the same meaning as cellular transduction of the gene. At the tissue level, the term gene delivery has the same meaning as spread of the gene. Thus, the gene delivery system of the present invention may be described as the gene transduction system and the gene spread system.

To prepare the gene delivery system of the present invention, the nucleotide sequence of the present invention is preferably present within a suitable expression construct. In the expression construct, it is preferable that the nucleotide sequence of the present invention is operatively linked to a promoter. As used herein, the term "operatively linked to" means a functional binding between a regulatory sequence of nucleic acid expression (for example, a promoter, a signal sequence, or an array at a transcription regulatory factor binding site) with other nucleic acid sequences, and the regulatory sequence thus regulates transcription and/or translation of the other nucleic acid sequences. In the present invention, a promoter, which binds to the nucleotide sequence of the present invention, may be operated preferably in animal cells, and more preferably in mammalian cells to regulate transcription of relaxin gene, and includes, but not limited to a promoter derived from mammalian virus and a promoter derived from a genome of mammalian cells such as mammalian cytomegalovirus (CMV) promoter, adenovirus late promoter, vaccinia virus 7.5K promoter, SV40 promoter, tk promoter of HSV, RSV promoter, EF1 alpha promoter, metallothionein promoter, beta-actin promoter, a promoter of human IL-2 gene, a promoter of human IFN gene, a promoter of human IL-4 gene, a promoter of human lymphotoxin gene, a promoter of human GM-CSF gene, and U6 promoter.

The gene delivery system of the present invention may be constructed in various forms which are (i) a naked recombinant DNA molecule, (ii) a plasmid, (iii) a virus vector, and (iv) a liposome or a noisome form including the naked recombinant DNA molecule or the plasmid.

The nucleotide sequence of the present invention may be applied to whole gene delivery system used for typical gene therapy. Preferably, the nucleotide sequence of the present invention may be applied to a plasmid, adenovirus (Lockett L J, et al., *Clin. Cancer Res.* 3:2075-2080(1997)), adeno associated virus (AAV, Lashford L S., et al., *Gene Therapy Technologies, Applications and Regulations* Ed. A. Meager, 1999), retrovirus (Gunzburg W H, et al., Retroviral vectors. *Gene Therapy Technologies, Applications and Regulations* Ed. A. Meager, 1999), lentivirus (Wang G. et al., *J. Clin. Invest.* 104(11):R55-62(1999)), herpes simplex virus (Chamber R., et al., *Proc. Natl. Act. Sci USA* 92:1411-1415 (1995)), vaccinia virus (Puhlmann M. et al., *Human Gene Therapy* 10:649-657(1999)), a liposome (Metho s in Molecular Biology, Vol 199, S. C. Basu and M. Basu (Eds.), Human Press 2002) or a niosome.

Most preferably, the nucleotide sequence of the present invention is delivered by using a cationic liposome.

According to another aspect of the present invention, the present invention provides a method for treating or preventing a disease associated with HPV infection, the method including administering, to a subject, a pharmaceutical composition including: (a) a pharmaceutically effective amount of one or more nucleotide sequences selected from the group consisting of sequences of SEQ ID Nos: 16, 22, 28, 34, 40, 66, 72, 84, 90, and 108 and antisense nucleotide sequences thereof; and (b) a pharmaceutically acceptable carrier.

According to another aspect of the present invention, the present invention provides a method for treating or preventing a disease associated with HPV infection, the method including administering, to a subject, a pharmaceutical composition including: (a) a pharmaceutically effective amount of one or more nucleotide sequences selected from the group consisting of sequences of SEQ ID Nos: 1, 7, 12, 16, 22, 28, 34, 40, 46, 51, 56, 62, 66, 72, 78, 84, 90, 96, 102 and 108, and antisense nucleotide sequences thereof which have a modified backbone or one or more modified bases; and (b) a pharmaceutically acceptable carrier.

According to another aspect of the present invention, the present invention provides a method for preventing or treating a disease associated with HPV infection, the method including administering, to a subject, a pharmaceutical composition including: (a) a pharmaceutically effective amount of nucleotide pool selected from the group consisting of: a pool having nucleotide sequences of SEQ ID Nos: 2, 4, 8, 9, 12, and 15; a pool having nucleotide sequences of SEQ ID Nos: 18, 21, 29, and 32; a pool having nucleotide sequences of SEQ ID Nos: 42, 45, 52, and 55; a pool having nucleotide sequences of SEQ ID Nos: 58, 59, 63 and 65; a pool having nucleotide sequences of SEQ ID Nos: 68, 71, 91 and 94; and a pool having nucleotide sequences of SEQ ID Nos: 98, 100, 109 and 112; and (b) a pharmaceutically acceptable carrier.

Since the method of the present invention uses the present composition described above, the features common to both the composition and the method are not described herein to avoid excessive complexity in the specification.

Advantageous Effects

The features and benefits of the present invention are summarized as follows:

(a) The present invention is to provide a composition for preventing or treating a disease associated with human papilloma virus (HPV) infection, more particularly, an HPV infection-associated cancer, and further more particularly a cervical cancer;

(b) The nucleotide sequence of the present invention, a sequence having a modification in a base of the nucleotide sequence, and particular combination thereof significantly inhibits expression of E6/E7 genes of HPV type 16 or HPV type 18 viruses, and is thus usefully employed as a composition or a method for efficiently treating a disease associated with HPV infection.

BRIEF DESCRIPTION OF THE DRAWINGS

FIGS. 2A-2B show images of results which verify an excellent effect of inducing cell senescence (FIG. 2A) and an excellent effect of killing cells (FIG. 2B) of siRNA having substituted residue in a base sequence of HPV 18 type.

FIGS. 4A, 4B, and 4C respectively show a cell-proliferation inhibiting effect, a cell-killing effect, and an effect at the molecular level of a protein.

FIGS. 5A and 5B respectively show an effect of reducing IL-6 on cells and an effect of reducing INF-gamma in animals.

FIGS. 8A, 8B, and 8C respectively show a variation in a size of a tumor of a mouse, an image of the tumor of the mouse, and a variation in body weight of the mouse.

MODE FOR CARRYING OUT THE INVENTION

Figure 1A:
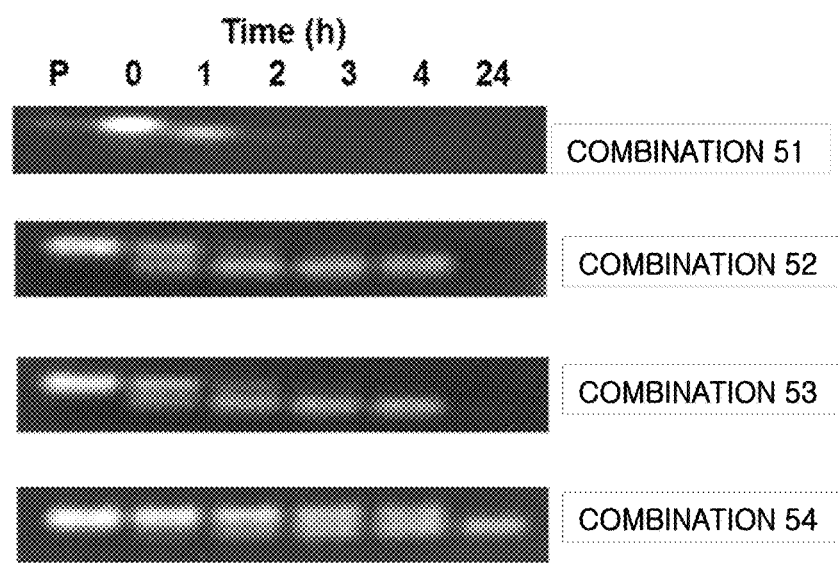
FIGS. 1A-1C show images of results which verify improvement in stability (FIG. 1A), an increase in an effect at the molecular level of a protein (FIG. 1B), and an increase in an effect at the molecular level of mRNA (FIG. 1C) according to a substitutional modification of a residue of a base sequence in siRNA of HPV 16, and 18 types.

Hereinafter, the present invention will be described in more detail with reference to examples. These examples are provided to only specifically describe the present invention, and it will be obvious to a person skilled in the art that the scope of the present invention is not limited to the examples according to the essential features of the present invention.

EXAMPLE

Experiment Method

Construction of siRNA of HPV 16, and 18 Types siRNAs in Tables 1 and 2 below are obtained from Bioneer corporation (Korea) through customized production. In the table below, the underlined siRNA sequence indicates a nucleotide substituted with a 2'-O-Me modified nucleotide in which a methyl group is bound to a residue of the base, and the thick italicized sequence indicates a base substituted with 2'-F modified nucleotide in which a hydroxyl group of a residue of the base is substituted with fluoro.

TABLE 1 siRNA to HPV 16 type

| SEQ. ID. No. | Sequence | Note |
|---|---|---|
| sequence 1 | 5'-GCA AAG ACA UCU GGA CAA A-3' | HPV 16 Type siRNA 366 |
| sequence 2 | 5'-GCA AAG ACA UC<u>U</u> <u>GGA</u> CAA A-3' | |
| sequence 3 | 5'-<u>GCA</u> AA<u>G</u> ACA UCU <u>GGA</u> CAA A-3' | |

TABLE 1-continued siRNA to HPV 16 type

| SEQ. ID. No. | Sequence | Note |
|---|---|---|
| sequence 4 | 5'-UUU GUC CAG AUG UCU UUG C-3' | |
| sequence 5 | 5'-UUU G̲UC CA̲G AUG UCU UUG C-3' | |
| sequence 6 | 5'-U̲UU GUC CAG AU̲G UCU UUG C-3' | |
| sequence 7 | 5'-UCA AGA ACA CGU AGA GAA A-3' | HPV 16 Type siRNA 448 |
| sequence 8 | 5'-UCA A̲GA ACA C̲GU A̲GA G̲AA A-3' | |
| sequence 9 | 5'-UUU CUC UAC GUG UUC UUG A-3' | |
| sequence 10 | 5'-UUU CUC UAC G̲UG UUC UUG A-3' | |
| sequence 11 | 5'-U̲UU CUC UAC GUG UUC U̲UG A-3' | |
| sequence 12 | 5'-GAC CGG UCG AUG UAU GUC UUG-3' | HPV 16 Type siRNA 497 |
| sequence 13 | 5'-GAC CGG U̲CG AUG U̲AU GUC U̲UG-3' | |
| sequence 14 | 5'-AGA CAU ACA UCG ACC GGU CCA-3' | |
| sequence 15 | 5'-AGA CAU̲ ACA U̲CG ACC GGU̲ CCA-3' | |
| sequence 16 | 5'-GGA GCG ACC CAG AAA GTT A-3' | HPV 16 Type siRNA 39 |
| sequence 17 | 5'-GGA G̲CG ACC CAG̲ AAA G̲TT A-3' | |
| sequence 18 | 5'-GGA G̲C̲G A̲C̲C̲ C̲AG AAA GTT A-3' | |
| sequence 19 | 5'-UAA CUU UCU GGG UCG CUC C-3' | |
| sequence 20 | 5'-UAA CU̲U UCU̲ GGG U̲CG CU̲C C-3' | |
| sequence 21 | 5'-UAA CUU UCU G̲GG UCG CU̲G C-3' | |
| sequence 22 | 5'-CAG AAA GTT ACC ACA GTT A-3' | HPV 16 Type siRNA 48 |
| sequence 23 | 5'-CAG̲ AAA G̲TT ACC ACA G̲TT A-3' | |
| sequence 24 | 5'-C̲AG AAA GTT AC̲C̲ AC̲A GTT A-3' | |
| sequence 25 | 5'-UAA CUG UGG UAA CUU UCU G-3' | |
| sequence 26 | 5'-UAA CUG̲ UGG U̲AA CU̲U UCU̲ G-3' | |
| sequence 27 | 5'-UAA CUG̲ UG̲G UAA CUU UCU G̲-3' | |
| sequence 28 | 5'-GCA CAG AGC TGC AAA CAA C-3' | HPV 16 Type siRNA 68 |
| sequence 29 | 5'-G̲CA CAG̲ AGC T̲GC AAA CAA C-3' | |
| sequence 30 | 5'-G̲C̲A CAG AG̲C̲ TG̲C̲ AAA C̲AA C-3' | |
| sequence 31 | 5'-GUU GUU UGC AGC UCU GUG C-3' | |
| sequence 32 | 5'-GU̲U GU̲U UGC AGC U̲CU GU̲G C-3' | |
| sequence 33 | 5'-GUU G̲UU UGC A̲GC UCU G̲UG C-3' | |
| sequence 34 | 5'-GCA AAC AAC TAT ACA TGA T-3' | HPV 16 Type siRNA 78 |
| sequence 35 | 5'-G̲CA AAC AAC TAT ACA T̲GA T-3' | |
| sequence 36 | 5'-G̲C̲A AA̲C̲ AA̲C̲ TAT AC̲A TGA T-3' | |
| sequence 37 | 5'-AUC AUG UAU AGU UGU UUG C-3' | |

TABLE 1-continued

| siRNA to HPV 16 type | | |
|---|---|---|
| SEQ. ID. No. | Sequence | Note |
| sequence 38 | 5'-AUC AUG UAU AGU UGU UUG C-3' | |
| sequence 39 | 5'-AUC AUG UAU AGU UGU UUG C-3' | |
| sequence 40 | 5'-AGC AAA GAC ATC TGG ACA A-3' | HPV 16 Type siRNA 365 |
| sequence 41 | 5'-AGC AAA GAC ATC TGG ACA A-3' | |
| sequence 42 | 5'-AGC AAA GAC ATC TGG ACA A-3' | |
| sequence 43 | 5'-UUG UCC AGA UGU CUU UGC U-3' | |
| sequence 44 | 5'-UUG UCC AGA UGU CUU UGC U-3' | |
| sequence 45 | 5'-UUG UCC AGA UGU CUU UGC U-3' | |
| sequence 46 | 5'-CAC CUA CAU UGC AUG AAU AUA-3' | HPV 16 Type siRNA 573 |
| sequence 47 | 5'-CAC CUA CAU UGC AUG AAU AUA-3' | |
| sequence 48 | 5'-UAU AUU CAU GCA AUG UAG GUG-3' | |
| sequence 49 | 5'-UAU AUU CAU GCA AUG UAG GUG-3' | |
| sequence 50 | 5'-UAU AUU CAU GCA AUG UAG GUG-3' | |
| sequence 51 | 5'-CUU CGG UUG UGC GUA CAA AGC-3' | HPV 16 Type siRNA 792 |
| sequence 52 | 5'-CUU CGG UUG UGC GUA CAA AGC-3' | |
| sequence 53 | 5'-GCU UUG UAC GCA CAA CCG AAG-3' | |
| sequence 54 | 5'-GCU UUG UAC GCA CAA CCG AAG-3' | |
| sequence 55 | 5'-GCU UUG UAC GCA CAA CCG AAG-3' | |

TABLE 2

| siRNA to HPV 18 type | | |
|---|---|---|
| SEQ. ID. No. | Sequence | Note |
| sequence 56 | 5'-CAA CCG AGC ACG ACA GGA A-3' | HPV 18 Type siRNA 426 |
| sequence 57 | 5'-CAA CCG AGC ACG ACA GGA A-3' | |
| sequence 58 | 5'-CAA CCG AGC ACG ACA GGA A-3' | |
| sequence 59 | 5'-UUC CUG UCG UGC UCG GUU G-3' | |
| sequence 60 | 5'-UUC CUG UCG UGC UCG GUU G-3' | |
| sequence 61 | 5'-UUC CUG UCG UGC UCG GUU G-3' | |
| sequence 62 | 5'-CCA ACG ACG CAG AGA AAC A-3' | HPV 18 Type siRNA 450 |
| sequence 63 | 5'-CCA ACG ACG CAG AGA AAC A-3' | |
| sequence 64 | 5'-UGU UUC UCU GCG UCG UUG G-3' | |
| sequence 65 | 5'-UGU UUC UCU GCG UCG UUG G-3' | |

TABLE 2 -continued siRNA to HPV 18 type

| SEQ. ID. No. | Sequence | Note |
|---|---|---|
| sequence 66 | 5'-ACT GCA AGA CAT AGA AAT A-3' | HPV 18 Type siRNA 72 |
| sequence 67 | 5'-ACT GCA AGA CAT AGA AAT A-3' | |
| sequence 68 | 5'-ACT GCA AGA CT AGA AAT A-3' | |
| sequence 69 | 5'-UAU UUC UAU GUC UUG CAG U-3' | |
| sequence 70 | 5'-UAU UUC UAU GUC UUG CAG U-3' | |
| sequence 71 | 5'-UAU UUC UAU GUC UUG CAG U-3' | |
| sequence 72 | 5'-GTA TAT TGC AAG ACA GTA T-3' | HPV 18 Type siRNA 97 |
| sequence 73 | 5'-GTA TAT TGC AAG ACA GTA T-3' | |
| sequence 74 | 5'-GTA TAT TGC AAG ACA GTA T-3' | |
| sequence 75 | 5'-AUA CUG UCU UGC AAU AUA C-3' | |
| sequence 76 | 5'-AUA CUG UCU UGC AAU AUA C-3' | |
| sequence 77 | 5'-AUA CUG UCU UGC AAU AUA C-3' | |
| sequence 78 | 5'-GCA AGA CAG TAT GGA ACT-3' | HPV 18 Type siRNA 103 |
| sequence 79 | 5'-GCA AGA CAG TAT GGA ACT-3' | |
| sequence 80 | 5'-GCA AGA CAG TAT GGA ACT-3' | |
| sequence 81 | 5'-AGU UCC AAU ACU GUC UUG C-3' | |
| sequence 82 | 5'-AGU UCC AAU ACU GUC UUG C-3' | |
| sequence 83 | 5'-AGU UCC AAU ACU GUC UUG C-3' | |
| sequence 84 | 5'-ATT GGA ACT TAC AGA GGT A-3' | HPV 18 Type siRNA 113 |
| sequence 85 | 5'-ATT GGA ACT TAC AGA GGT A-3' | |
| sequence 86 | 5'-ATT GGA ACT TAC AGA GGT A-3' | |
| sequence 87 | 5'-UAC CUC UGU AAG UUC CAA U-3' | |
| sequence 88 | 5'-UAC CUC UGU AAG UUC CAA U-3' | |
| sequence 89 | 5'-UAC CUC UGU AAG UUC CAA U-3' | |
| sequence 90 | 5'-CTC AAC GAC GCA GAG AAA A-3' | HPV 18 Type siRNA 448 |
| sequence 91 | 5'-CTC AAC GAC GCA GAG AAA A-3' | |
| sequence 92 | 5'-CTC AAC GAC GCA GAG AAA A-3' | |
| sequence 93 | 5'-UUU CUC UGC GUC GUU GGA G-3' | |
| sequence 94 | 5'-UUU CUC UGC GUC GUU GGA G-3' | |
| sequence 95 | 5'-UUU CUC UGC GUC GUU GGA G-3' | |
| sequence 96 | 5'-ACG CAG AGA AAC ACA AGT A-3' | HPV 18 Type siRNA 456 |
| sequence 97 | 5'-ACG CAG AGA AAC ACA AGT A-3' | |
| sequence 98 | 5'-ACG CAG AGA AAC ACA AGT A-3' | |
| sequence 99 | 5'-UAC UUG UGU UUC UCU GCG U-3' | |

TABLE 2 -continued siRNA to HPV 18 type

| SEQ. ID. No. | Sequence | Note |
|---|---|---|
| sequence 100 | 5'-UAC UUG UGU UUC UCU GCG U-3' | |
| sequence 101 | 5'-UAC UUG UGU UUC UCU GCG U-3' | |
| sequence 102 | 5'-GCA GAG AAA CAC AAG TAT A-3' | HPV 18 Type siRNA 458 |
| sequence 103 | 5'-GCA GAG AAA CAC AAG TAT A-3' | |
| sequence 104 | 5'-GCA GAG AAA CAC AAG TAT A-3' | |
| sequence 105 | 5'-UAU ACU UGU GUU UCU CUG C-3' | |
| sequence 106 | 5'-UAU ACU UGU GUU UCU CUG C-3' | |
| sequence 107 | 5'-UAU ACU UGU GUU UCU CUG C-3' | |
| sequence 108 | 5'-CAG AGA AAC ACA AGT ATA A-3' | HPV 18 Type siRNA 459 |
| sequence 109 | 5'-CAG AGA AAC ACA AGT ATA A-3' | |
| sequence 110 | 5'-CAG AGA AAC ACA AGT ATA A-3' | |
| sequence 111 | 5'-UUA UAC UUG UGU UUC UCU G-3' | |
| sequence 112 | 5'-UUA UAC UUG UGU UUC UCU G-3' | |
| sequence 113 | 5'-UUA UAC UUG UGU UUC UCU G-3' | |

Evaluation of Stability of siRNA siRNA was mixed with 10% fetal bovine serum or 10% human serum while staying at 37☐, and samples were taken in a time based manner. Then, samples were quick frozen and stored at −70☐. Collected samples were subjected to electrophoresis for one and a half hours on 12% polyacrylamide gel at 50 V followed by Et-Br staining for UV measurement.

Cell Culture and Transduction of siRNA

A cervical cancer cell, a HeLa cervical cancer cell line (ATCC CCL-2) infected with HPV 18 type virus, or SiHa (ATCC HTB-35) or CaSki (ATCC CRL-1550) cervical cancer cell line infected with HPV 16 type virus was seeded on a 6-well plate in the cell number of $2 \times 10^5$ or $1.6 \times 10^5$, and respectively cultured in RPMI1640 or DMEM medium having 10% fetal bovine serum added thereto for 24 hours under the condition of 37☐, and 5% $CO_2$. After culturing for 24 hours in the medium to attach cells to a surface of the culture plate, unmodified siRNA as a control and an siRNA oligonucleotide modified by the method described above as an experimental group (20 nM for each), were transduced by using DharmaFECT 1 (Dharmacon, USA), and the resultant was cultured for 24 hours.

Anti-Cancer Agent Treatment

A HeLa or Caski cell line, which was seeded in a 6-well plate in $2 \times 10^5$ cells or $1.5 \times 10^5$ cells and then cultured for a day by the method as described above, was transduced with siRNA. Then, each transduced cell line was treated with cisplatin (CDDP) in a final concentration of 2.5 uM, and cultured.

Cell Senescence-Associated β-Galactosidase (SA-β-Gal) Activity Measurement

By the method as described above, a HeLa or Caski cell line was transduced with siRNA, alone or in combination with an anti-cancer agent, and then cultured for a day. By using the cell senescence assay kit (BioVision, USA), cells were washed with PBS and treated with SA-β-gal staining solution for 12 hours at 37☐. Cells stained in blue were observed by using a general optical microscope with the magnification of 100 to 200 times.

Measurement of Cell Death by Using Flow Cytometry

By the method as described above, a HeLA or Caski cell line was transduced with siRNA, alone or in combination with an anti-cancer agent, and then cultured for a day. The cells were stained with and reacted to Annexin V and propidium iodide (PI) reagents for 30 minutes at room temperature by using cell death assay kit (BD, USA), and thereafter cell death was evaluated by using a flow cytometry.

Investigation of Influence of siRNA Treatment

By the method as described above, a HeLA or Caski cell line was transduced with siRNA, alone or in combination with an anti-cancer agent, and then cultured for a day. To observe a change in a protein, cells were disrupted by adding RIPA cell lysis buffer [150 mM NaCl, 10 mM Tris-HCl (pH 7.4), 5 mM EDTA, 0.1% SDS, 0.5% deoxycholate and 1% NP-40]. Then, variation in protein level was observed through the general western-blot method. Anti-TP53, anti-E7, and anti-actin mouse antibody were purchased from Santa Cruz (USA), diluted to 1:1000, and used. The goat anti-mouse IgG HRP conjugated antibody was purchased from Jackson Laboratories (USA), diluted to 1:3000, and used.

Further, to observe variation in mRNA level, cells were disrupted by using a Trizol solution (Invitrogen, USA), and RNA was detected passing through ethanol purification to thereby observe variation in mRNA level through the general real-time polymerase chain reaction (PCR) method.

Investigation of Influence of Off-Target Effect of siRNA

A HeLA or Caski cell line was seeded on a 6-well plate, and respectively cultured for 24 hours in RPMI1640 or DMEM medium having 10% fetal bovine serum under the condition of 37□, and 5% $CO_2$. β-gal siRNA, which was a positive control, and siRNA were transduced and cultured, and then the medium was collected to perform the general IL-6 (BD, USA) ELISA method.

A mouse at the age of 6 weeks was intravenously injected with β-gal siRNA as a positive control, siRNA as a negative control, and siRNA, and the reaction was proceeded for 6 hours. Thereafter, blood was collected from the mouse, and serum was separated to perform INF-gamma (BD, USA) ELISA.

Stem-Loop Real-Time PCR to Quantify siRNA

A rat weighing about 260 to 300 g (at the age of 4 weeks) was intravenously injected with siRNA, and then blood of the rat was collected to separate plasma. The separated plasma was diluted in 0.25% triton X-100 buffer. cDNA was synthesized by using Taqman microRNA Reverse Transcription kit (Applied Biosystem, USA), and quantified by the real-time PCR method to detect siRNA.

Animal Test of siRNA

A female nude mouse was xenografted with $5 \times 10^6$ of HeLa cells of HPV 18 type, and generation of cancer cells was evaluated 10 days later. Then, 3 mg/kg of siRNA to be used was intravenously injected to tails at the 2-3 day interval. Cisplatin (2 mg/kg) and paclitaxel (4 mg/kg) were repeatedly injected 9 times by an intraperitoneal injection at 3-4 day interval. The size of a tumor was measured at 2-3 day interval.

Experimental Result

Variation in siRNA Treatment Concentration and Treatment Number

For a Caski or HeLa cell line infected with HPV 16 or 18 type, when performing siRNA transduction and an anticancer agent treatment, alone or in combination, in conventional technique, efficacy of siRNA was showed in successive treatment for long period at a high concentration (100 nM), while the modified siRNA of the present invention exhibited excellent efficacy in single treatment for short period at a low concentration (20 nM).

Stability Test of siRNA Having Substituted Residue siRNAs of combination 51 to 54, obtained by the method described above, were mixed with 10% human serum. Then, each siRNA was taken in a time-based manner at the temperature of 37□, and stored at −70□. Thereafter, gel electrophoresis was performed on 12% polyacrylamide gel. The resultant was stained with Et-Br, and measured with UV. Consequently, as shown in FIG. 1a, siRNA of combination 51 having an unsubstituted residue in a base sequence was disappeared within two hours, while siRNAs of combination 52 to 54 having substituted residue in a base sequence were remained at least 4 hours, indicating a considerable increase in stability. In particular, combination showed the most outstanding stability which lasts over 24 hours.

Effect of siRNA Having Substituted Residue at the Molecular Level

Figure 1B:
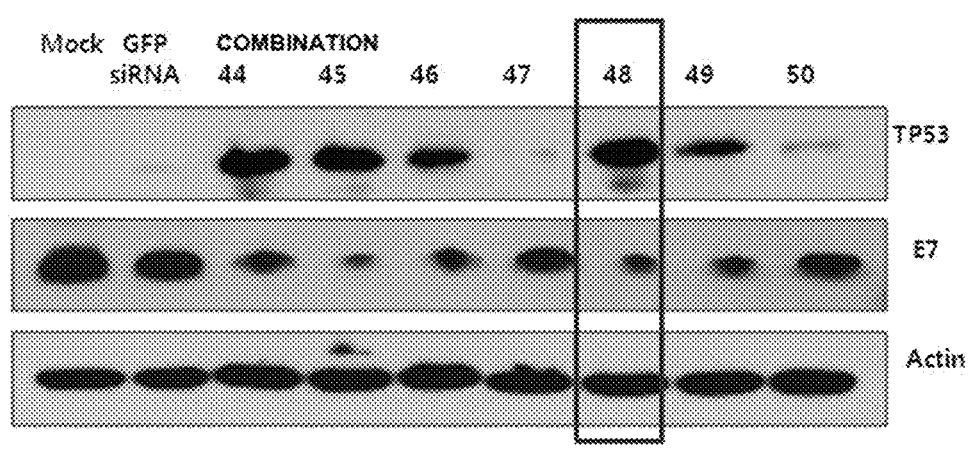

By the method described above, a HeLa cell line was transduced with siRNAs of combination 44 to 50, mock and GFP siRNA, and then variation in TP 53, and E7 protein levels was evaluated, while using actin as a housekeeping gene, wherein siRNAs of combination 44 to 50 were siRNAs of HPV 18 type, and mock and GFP were controls. As shown in FIG. 1b, variation in TP53 and E7 protein level of combination 44 was compared with that of combination 45 to 50, wherein combination 44 has an unsubstituted residue in a base sequence, and combination 45 to 50 has a substituted residue in a base sequence. It was proven that efficacy of combination 48 to increase TP53 protein expression and to reduce E7 protein expression was superior to other sequences.

Figure 1C:
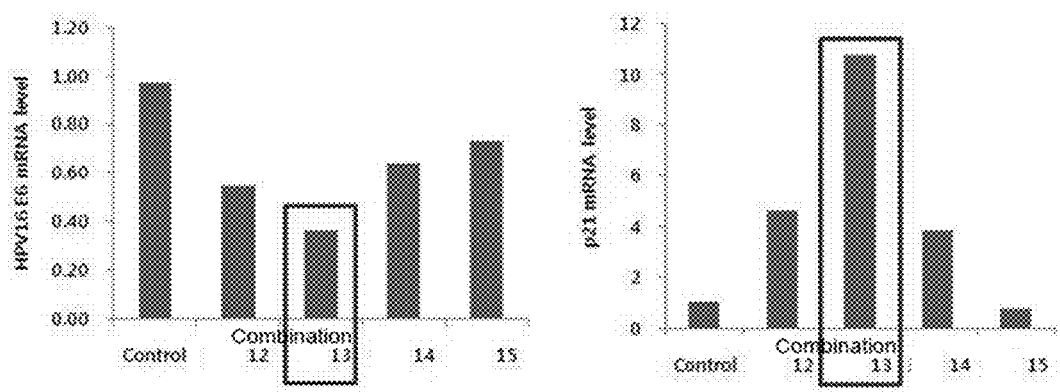

Further, for siRNA 497 of HPV 16 type, a Caski cell line was transduced with combination 12 to 15 by the method described above, and then mRNA was extracted to evaluate mRNA expression levels of E6 and P21. Consequently, as shown in FIG. 1c, it has been proven that combination 13 reduced by 60% or more of E6 mRNA and increased by 1100% or more of p21 mRNA with respect to the control, wherein, combination 13 has a substituted residue in a base sequence. It has been also evaluated that combination 13 was superior to other sequences comparing with combination 12 which has an unsubstituted residue in a base sequence.

Cell Senescence-Inducing Effect of siRNA Having Substituted Residue

Figure 2A:
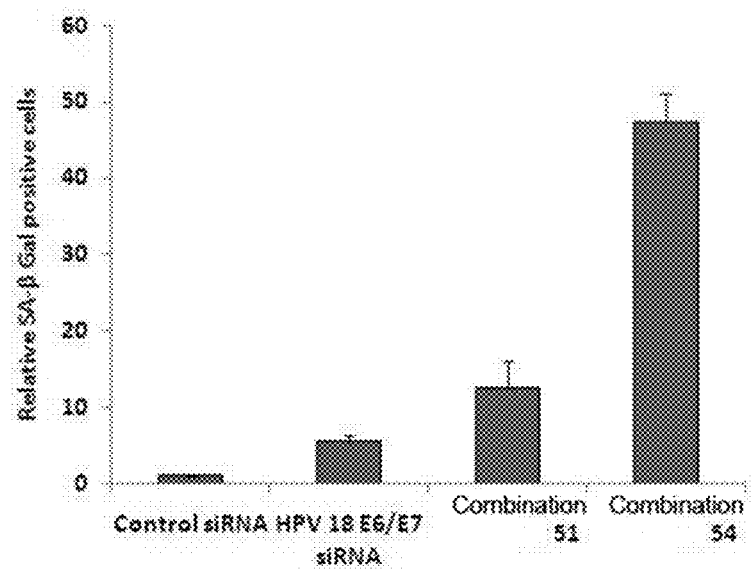

SA β-Gal activity of a HeLA or Caski cell line, which was treated by the method as described above, was measured. Consequently, in FIG. 2a, in the cases where HPV 18E6/E7 siRNA and combination 51 were transduced, the SA-β Gal activity was incased by about 10 to 20 times, while the SA-β Gal activity for combination 54 was increased by 50 times or more comparing with that of the control siRNA, wherein HPV 18E6/E7 siRNA was used in the previous invention; combination 51 consisted of 450 siRNA having an unsubstituted residue in a base sequence; and combination 54 consisted of siRNA having a substituted residue in a base sequence. The result showed that the cell senescence effect of combination 54 having substation in a base sequence was considerably better than that of combination 51 having no substitution of a base sequence.

Cell-Killing Effect of siRNA Having Substituted Residue

By the method described above, a cell-killing effect was measured by using a flow cytometry. As a result obtained by evaluating the cell-killing effect by comparing HPV 18E6/E7, 18E6 siRNA, combination 48, and combination 54 (which have a substituted residue in a base sequence) with the control, it has been proven that HPV 18E6/E7 and 18E6 siRNA groups showed cell-killing effect of only 15 to 20%, while siRNA groups having a substituted residue showed about 60% or more of cell-killing effect, with respect to the control (FIG. 2b). The result showed that siRNA sequences having substitution in a base sequence showed more significant cancer cell-killing effect than typical siRNA.

Effect of Combined Treatment of Cisplatin and siRNA Having Substituted Residue

Figure 3A:
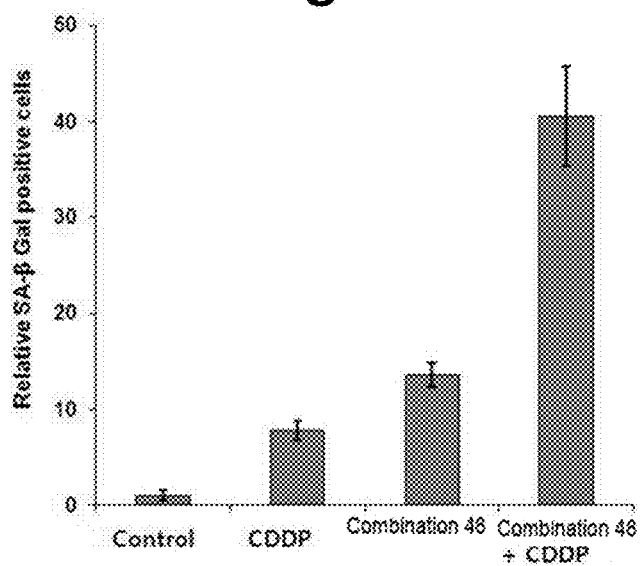
FIGS. 3A-3B are images showing the effect of inducing cell senescence by combined treatment of the anti-cancer agent, cisplatin, and 426 siRNA having a substitution in a base sequence in a HeLa cervical cancer cell line infected with the HPV 18 type virus (FIG. 3A) and a microscopically observed result thereof (FIG. 3B).
Figure 3B:
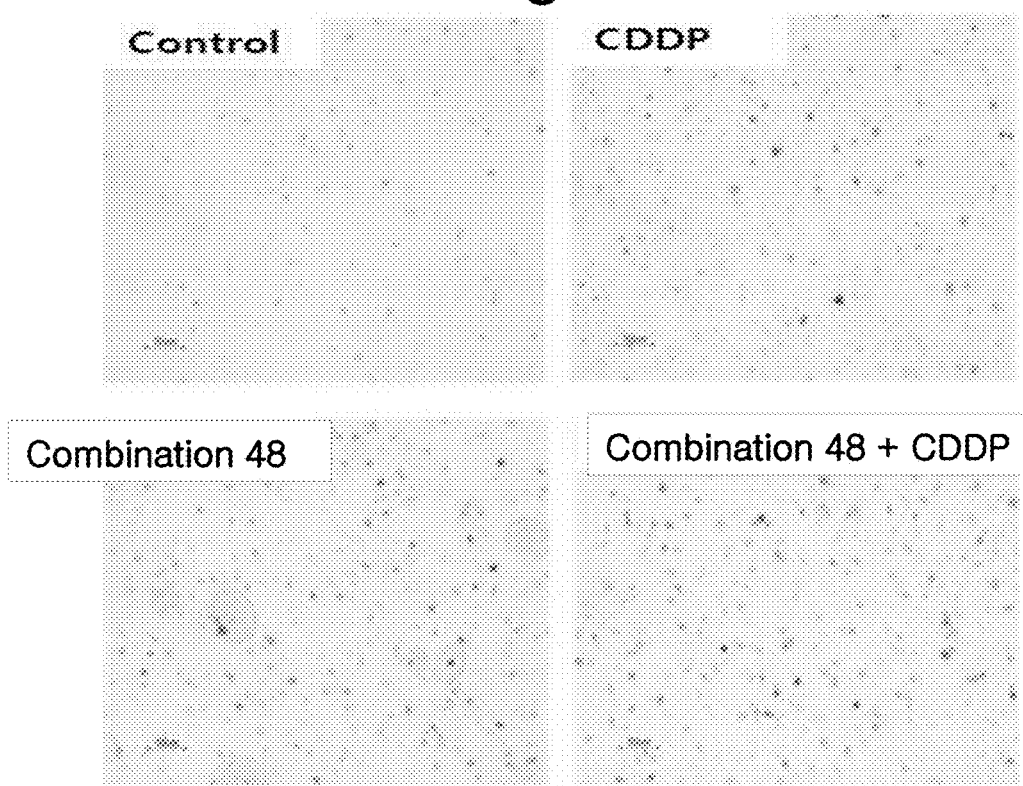

As a result of measuring SA β-Gal activity by treating a HeLa cell line with cisplatin and combination 48 having a substituted residue in a base sequence by the method as described above, as shown in FIGS. 3a and 3b, cells were stained in blue in cell lines respectively treated with cisplatin and combination 48 alone, showing SA β-Gal activity. However, almost of cells were stained in dark blue which indicates strong SA β-Gal activity for the combined treatment group of combination 48 and cisplatin. The result showed that the combined treatment group exhibited much superior cell senescence effect to the mono-treatment group of siRNA or cisplatin.

Figure 4A:
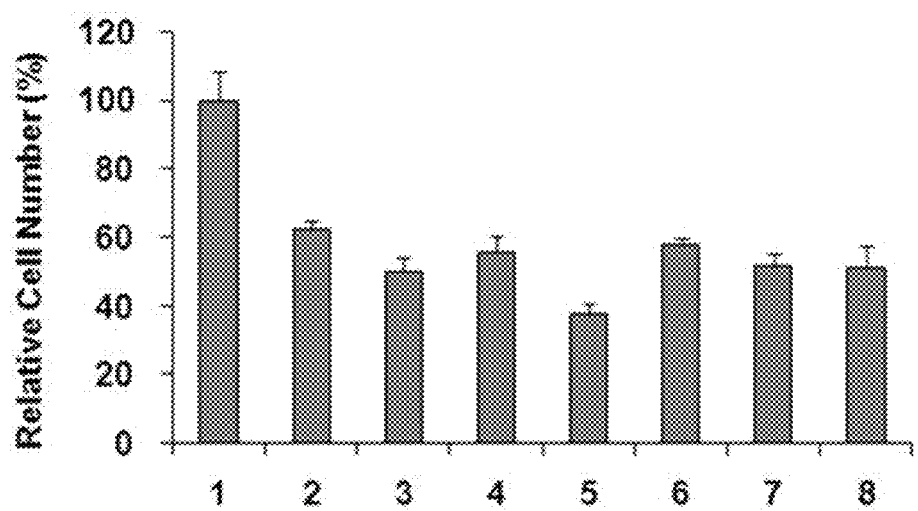
FIGS. 4A-4C show images of results which verify a therapeutic effect of a pool of excellent siRNA having a substitution in a base sequence of HPV 16, and 18 types, and a synergetic effect by combined therapy with cisplatin.

Effect of Inhibiting Cell Proliferation by Mono-Treatment or Combined Treatment of siRNA Pool By the method described above, HPV 16 type Caski cell lines were respectively treated with 20 mM of siRNA combination 2, 9, and 13 alone, wherein the siRNA combination 2, 9, and 13 has substitution in a base sequence of HPV 16 type, and HPV 16 type Caski cell lines were transduced with: the pool of combination 2 and combination 9 (10 nM, for each); the pool combination 2 and combination 13 (10 nM, for each); the pool of combination 9 and combination 13 (10 nM, for each); and pool of combination 2, combination 9, and combination 13 (7 nM, for each). Then, cell number was measured 24 hours later. Consequently, as shown FIG. 4a, cell proliferation was reduced in the mono treatment groups of each siRNA having substitution in a base sequence, and the siRNA pool treatment group in a similar manner. Particularly, although each siRNA was treated in an amount of 7 nM, the pool of 3 types of siRNA showed the effect equivalent to the case where 20 nM of each siRNA was treated.

Combination of the siRNA pool used herein was shown in Table 3 below, and siRNA pool shown in Table 4 below includes a mixture of two or more of combination having particularly higher cell proliferation inhibiting effects.

TABLE 3

Combination of siRNA

| Number of combination | Sense | Antisense | note |
|---|---|---|---|
| combination 1 | sequence 1 | sequence 4 | HPV 16 type |
| combination 2 | sequence 2 | sequence 4 | siRNA 366 |
| combination 3 | sequence 2 | sequence 5 | |
| combination 4 | sequence 2 | sequence 6 | |
| combination 5 | sequence 3 | sequence 4 | |
| combination 6 | sequence 3 | sequence 5 | |
| combination 7 | sequence 3 | sequence 6 | |
| combination 8 | sequence 7 | sequence 9 | HPV 16 type |
| combination 9 | sequence 8 | sequence 9 | siRNA 448 |
| combination 10 | sequence 8 | sequence 10 | |
| combination 11 | sequence 8 | sequence 11 | |
| combination 12 | sequence 12 | sequence 14 | HPV 16 type |
| combination 13 | sequence 12 | sequence 15 | siRNA 497 |
| combination 14 | sequence 13 | sequence 14 | |
| combination 15 | sequence 13 | sequence 15 | |
| combination 16 | sequence 16 | sequence 19 | HPV 16 Type |
| combination 17 | sequence 17 | sequence 20 | siRNA 39 |
| combination 18 | sequence 18 | sequence 21 | |
| combination 19 | sequence 18 | sequence 21 | |
| combination 20 | sequence 22 | sequence 25 | HPV 16 Type |
| combination 21 | sequence 23 | sequence 25 | siRNA 48 |
| combination 22 | sequence 24 | sequence 26 | |
| combination 23 | sequence 24 | sequence 27 | |
| combination 24 | sequence 28 | sequence 31 | HPV 16 Type |
| combination 25 | sequence 29 | sequence 32 | siRNA 68 |
| combination 26 | sequence 30 | sequence 32 | |
| combination 27 | sequence 30 | sequence 33 | |
| combination 28 | sequence 34 | sequence 34 | HPV 16 Type |
| combination 29 | sequence 35 | sequence 37 | siRNA 78 |
| combination 30 | sequence 36 | sequence 38 | |
| combination 31 | sequence 36 | sequence 39 | |
| combination 32 | sequence 40 | sequence 43 | HPV 16 Type |
| combination 33 | sequence 41 | sequence 44 | siRNA 365 |
| combination 34 | sequence 42 | sequence 44 | |
| combination 35 | sequence 42 | sequence 45 | |
| combination 36 | sequence 46 | sequence 48 | HPV 16 Type |
| combination 37 | sequence 46 | sequence 49 | siRNA 573 |
| combination 38 | sequence 47 | sequence 48 | |
| combination 39 | sequence 47 | sequence 50 | |
| combination 40 | sequence 51 | sequence 53 | HPV 16 Type |
| combination 41 | sequence 51 | sequence 55 | siRNA 792 |
| combination 42 | sequence 52 | sequence 54 | |
| combination 43 | sequence 52 | sequence 55 | |
| combination 44 | sequence 56 | sequence 59 | HPV 18 type |
| combination 45 | sequence 57 | sequence 59 | siRNA 426 |
| combination 46 | sequence 57 | sequence 60 | |
| combination 47 | sequence 57 | sequence 61 | |
| combination 48 | sequence 58 | sequence 59 | |
| combination 49 | sequence 58 | sequence 60 | |
| combination 50 | sequence 58 | sequence 61 | |

TABLE 3-continued

Combination of siRNA

| Number of combination | Sense | Antisense | note |
|---|---|---|---|
| combination 51 | sequence 62 | sequence 64 | HPV 18 type |
| combination 52 | sequence 62 | sequence 65 | siRNA 450 |
| combination 53 | sequence 63 | sequence 64 | |
| combination 54 | sequence 63 | sequence 65 | |
| combination 55 | sequence 66 | sequence 69 | HPV 18 Type |
| combination 56 | sequence 67 | sequence 70 | siRNA 72 |
| combination 57 | sequence 67 | sequence 69 | |
| combination 58 | sequence 68 | sequence 71 | |
| combination 59 | sequence 72 | sequence 76 | HPV 18 Type |
| combination 60 | sequence 73 | sequence 75 | siRNA 97 |
| combination 61 | sequence 73 | sequence 77 | |
| combination 62 | sequence 74 | sequence 77 | |
| combination 63 | sequence 78 | sequence 83 | HPV 18 Type |
| combination 64 | sequence 79 | sequence 82 | siRNA 103 |
| combination 65 | sequence 80 | sequence 81 | |
| combination 66 | sequence 80 | sequence 82 | |
| combination 67 | sequence 84 | sequence 89 | HPV 18 Type |
| combination 68 | sequence 85 | sequence 87 | siRNA 113 |
| combination 69 | sequence 86 | sequence 88 | |
| combination 70 | sequence 86 | sequence 89 | |
| combination 71 | sequence 90 | sequence 95 | HPV 18 Type |
| combination 72 | sequence 91 | sequence 94 | siRNA 448 |
| combination 73 | sequence 92 | sequence 93 | |
| combination 74 | sequence 92 | sequence 95 | |
| combination 75 | sequence 96 | sequence 99 | HPV 18 Type |
| combination 76 | sequence 97 | sequence 99 | siRNA 456 |
| combination 77 | sequence 98 | sequence 100 | |
| combination 78 | sequence 98 | sequence 101 | |
| combination 79 | sequence 102 | sequence 107 | HPV 18 Type |
| combination 80 | sequence 103 | sequence 106 | siRNA 458 |
| combination 81 | sequence 103 | sequence 107 | |
| combination 82 | sequence 104 | sequence 105 | |
| combination 83 | sequence 108 | sequence 113 | HPV 18 Type |
| combination 84 | sequence 109 | sequence 112 | siRNA 459 |
| combination 85 | sequence 110 | sequence 112 | |
| combination 86 | sequence 110 | sequence 113 | |

TABLE 4 siRNA Pool

| Number of pool | Sense | Antisense | Number of combination | Note |
|---|---|---|---|---|
| SP1 | sequence 2 | sequence 4 | 2 | HPV 16 type |
| | sequence 8 | sequence 9 | 9 | siRNAs 366/ |
| | sequence 12 | sequence 15 | 13 | 448/497 |
| SP2 | sequence 18 | sequence 21 | 18 | HPV16 type |
| | sequence 29 | sequence 32 | 25 | siRNAs 39/68 |
| SP3 | sequence 42 | sequence 45 | 35 | HPV16 type |
| | sequence 52 | sequence 55 | 43 | siRNAs 365/792 |
| SP4 | sequence 58 | sequence 59 | 48 | HPV 18 type |
| | sequence 63 | sequence 65 | 54 | siRNAs 426/450 |
| SP5 | sequence 68 | sequence 71 | 58 | HPV18 type |
| | sequence 91 | sequence 94 | 72 | siRNAs 72/448 |
| SP6 | sequence 98 | sequence 100 | 77 | HPV18 type |
| | sequence 109 | sequence 112 | 84 | siRNAs 456/459 |

Cell-Killing Effect of Mono-Treatment and Combined Treatment of siRNA Pool

By the method described above, an HPV 18 type HeLa cell line was treated with combination 48 and combination 54 (20 nm, for each) wherein, combination 48 and combination 20 have siRNA of HPV 18 type having substation in a base sequence, and transduced with the 10 nM of the SP4 pool, which is the pool of siRNA of 5 nM of combination 48 and 5 nM of combination 54. After 24 hours, the cell line was stained with Annexin V and propidium iodide, and cell-killing effect was measured by using a flow cytometry.

Figure 4B:
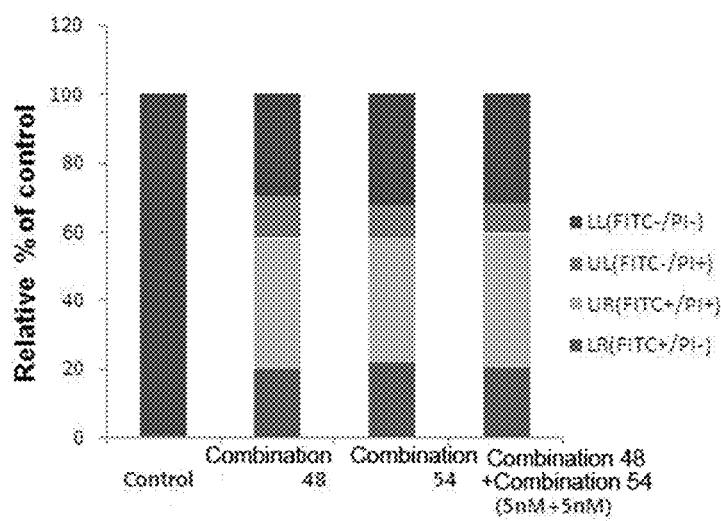

Consequently, as shown in FIG. 4b, both the mono-treatment groups of siRNA, which have substitution in a base sequence, and the siRNA pool (SP4) showed the effect of killing 80% or more of cells. As a result, it has been proven that 20 nM of the siRNA mono-treatment group showed the cell-killing effect similar to that of 10 nM of the siRNA pool, indicating that the siRNA pool was better.

Effect of siRNA Pool in Mono- and Combined Treatment at Molecular Level

Figure 4C:
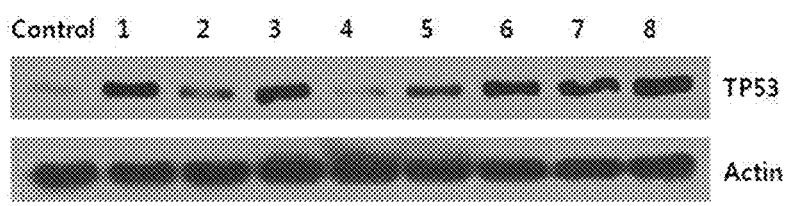

By the method described above, in a HPV 16 type CaSki cell line, the western-bolt method was used to compare a TP53 protein expression level for a combined treatment group of cisplatin and combination 2, 9, 13; a mono-treatment group of cisplatin; a combined treatment group of cisplatin and combination 2 and 9; a combined treatment group of cisplatin and combination 2 and 13; a combined treatment group of cisplatin and combination 9 and 13; and a combined treatment group of cisplatin and pool SP1 (a pool of combination 2, combination 9, and combination 13), wherein combination 2, 9, and 13 have substitution in a base sequence. Consequently, as shown in FIG. 4C, among combined treatment groups of siRNA pools and cisplatin, the highest increase in a TP53 protein expression level was shown in the pool SP1 which was treated with low concentration of 7 nM.

The result showed that since the pool selectively consisted of siRNA which was competent and efficient while mimicking features of naturally-occurring siRNA pool, it is possible to mix and use in a concentration lower than the concentration of the typical treatment, and reduce off-target effect.

Off-Target Effect of siRNA

Figure 5A:
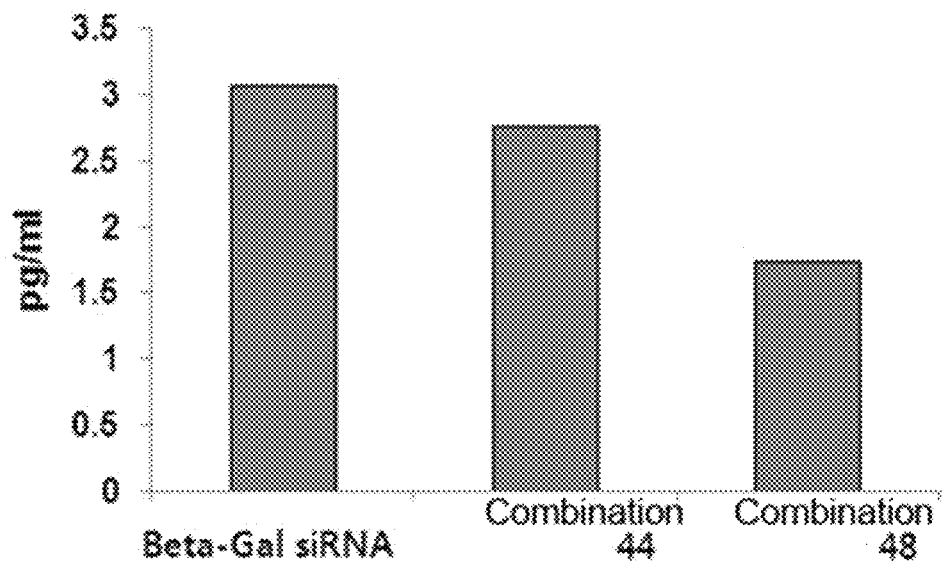
FIGS. 5A-5B show images of results which verify an off-target effect of siRNA of HPV 18 type in cells and animals.

By the method described above, HPV 18 type HeLa cell line was transduced with β-gal siRNA as a positive control, combination 44 having an unsubstituted residue, and combination 48 having a substituted residue in a base sequence. Then, an immune response experiment of IL-6 was performed. Consequently, as shown in FIG. 5a, immune response of IL-6 was increased in the positive control and combination 44, while immune response of IL-6 was reduced to ½ level of the positive control for combination 48 having a substituted residue in a base sequence.

Figure 5B:
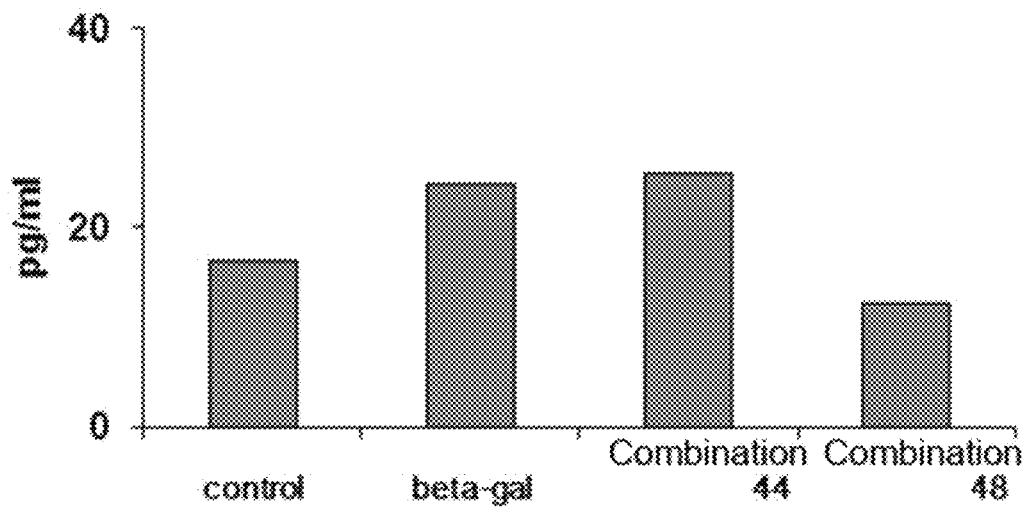

Further, a mouse at the age of 6 weeks was intravenously injected with β-gal siRNA and HPV 18 type siRNA combination 44 and 48 which arise immune response, and reacted for 6 hours to perform an immune response experiment of INF-gamma (FIG. 5b). Although immune response was observed in the positive control β-gal siRNA and combination 44 which was expressed by an increase in the INF-gamma level, immune response was not observed in combination 48 since INF-gamma in combination 48 showed a similar level to that of the negative control and did not increased.

Thus, it has been found that immune response was reduced in the siRNA treatment group having a substituted residue comparing with that siRNA having an unsubstituted residue does.

Pharmacokinetic Experiment of siRNA Having Substituted Residue

Figure 6:
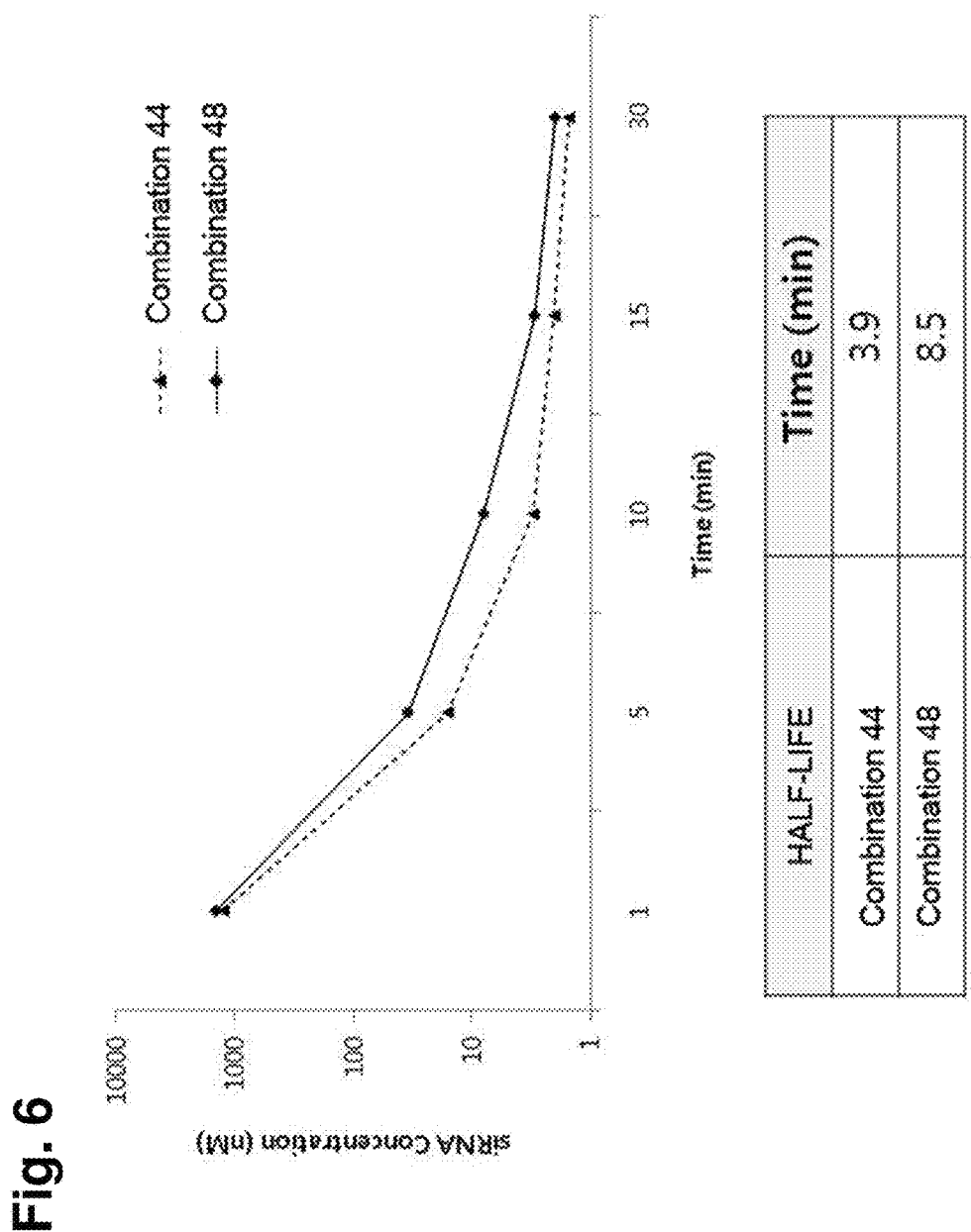
FIG. 6 shows an image of results which quantify 426 siRNA of HPV 18 type through stem-loop real-time PCT.

By the method described above, a rat was intravenously injected with HPV 18 type siRNA combination 44 and combination 48, and blood was collected in a time-based manner. Then, plasma was separated to quantify siRNA through stem-loop real-time PCR method. Consequently, as shown in FIG. 6a, half-life of combination 48 was at least twice longer than that of combination 44 meaning that combination 48, which has a substituted residue in a base sequence, is more stable in vivo.

Effect of siRNA in Various Types of Liposome

Figure 7:
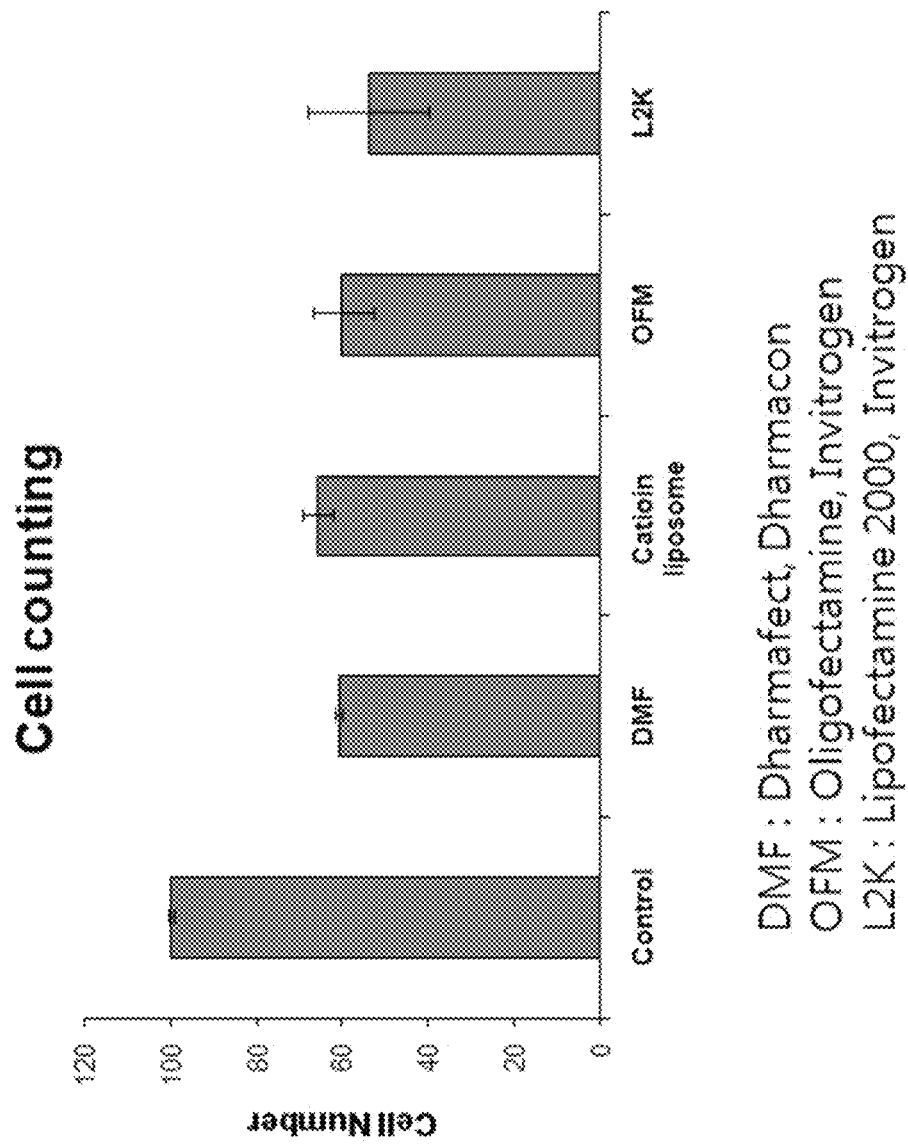
FIG. 7 shows an image of results which verify the fact that siRNAs in various types of liposomes show the same cell-killing effect on cells.

By the method described above, a HPV 18 type HeLa cell line was transduced with siRNA by using commercially available Dharmafect (Dharmacon), Oligofectamine and Lipofectamine 2000 (Invitrgen) drug delivery systems and a cationic liposome prepared by the present inventors. After 24 hours, cell number was measured to evaluate the effect of inhibiting cell proliferation. Consequently, as shown in FIG. 7a, siRNA was effectively delivered to a cell line infected with HPV in various drug delivery systems.

Effect of Combined Treatment of siRNA Pool and Anti-Cancer Agent

Figure 8A:
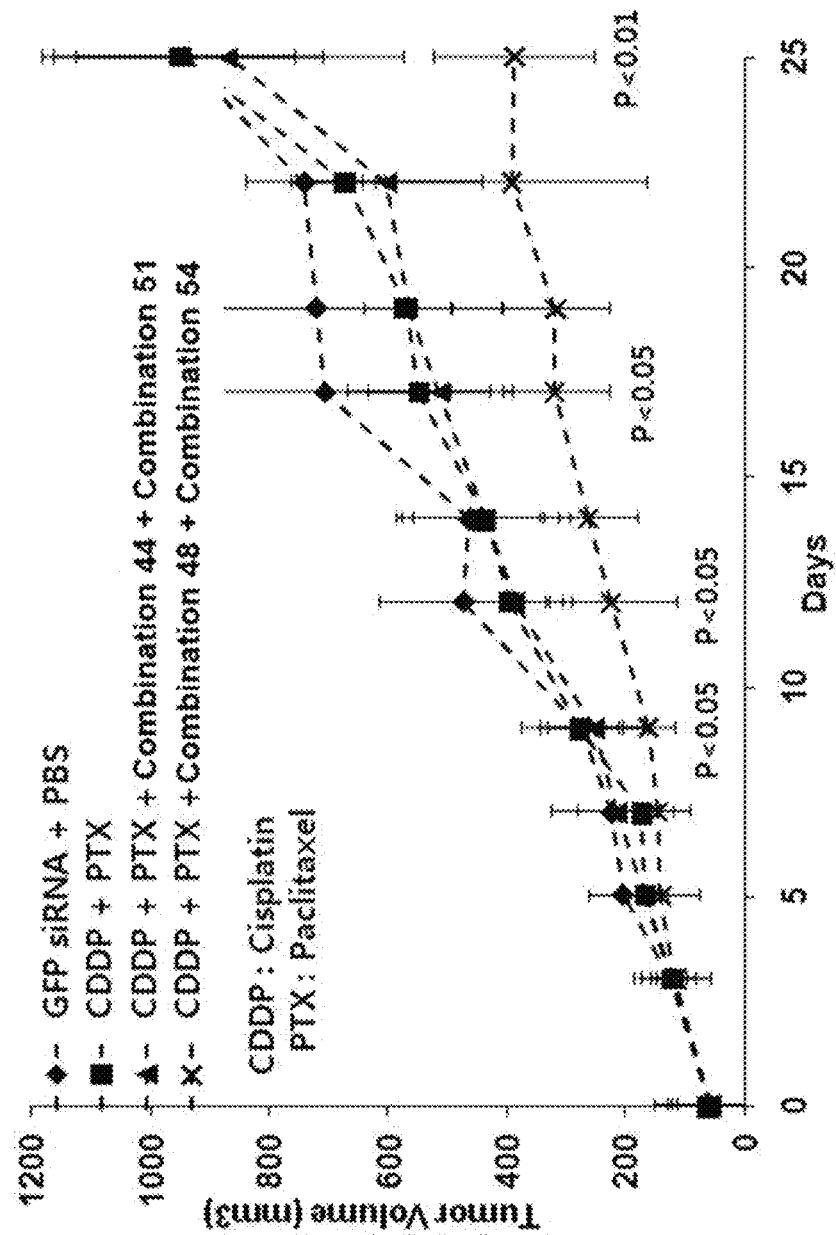
FIGS. 8A-8C are images showing a synergistic effect by combined treatment of an anti-cancer agent and a pool of siRNAs, which have a substitution in a base sequence and show the excellent effect, in an animal experiment.
Figure 8B:
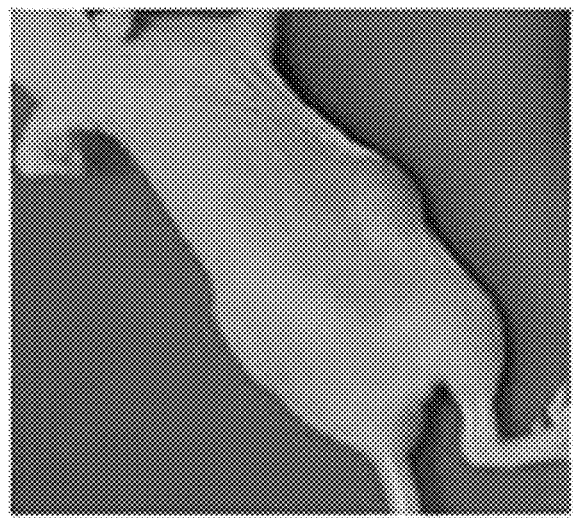
Figure 8B:
Figure 8C:
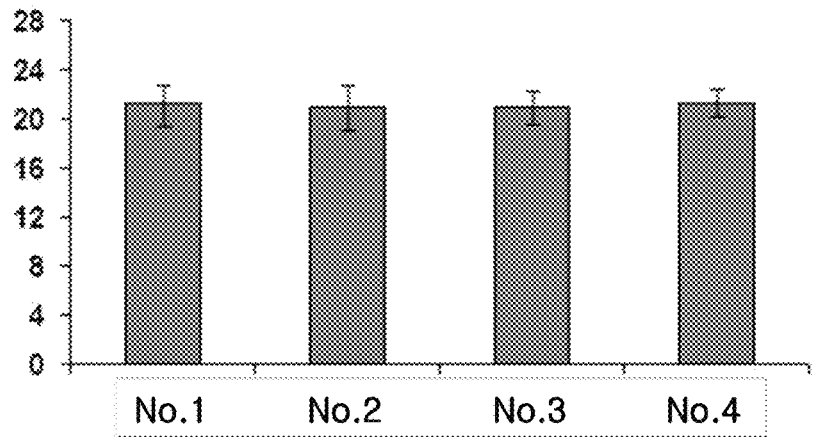
Figure 8C:
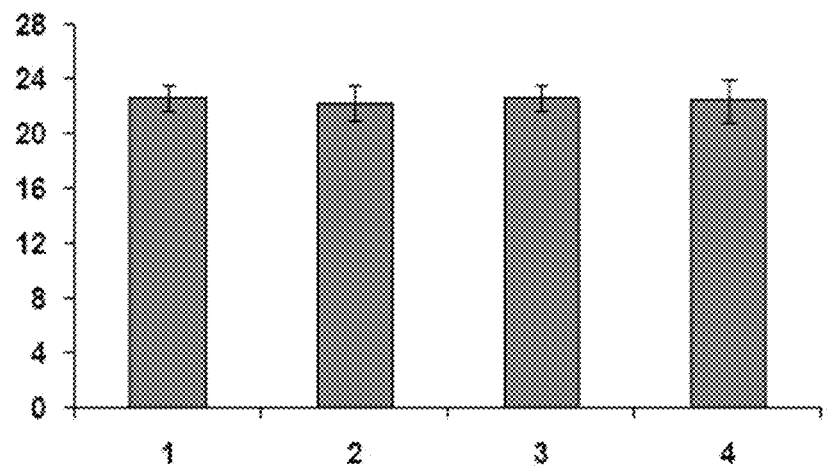

By the method described above, cancer cells were xenografted to a mouse. After 10 days, generation of cancer cells was evaluated. Then, siRNA and an anti-cancer agent were repeatedly injected 9 times, and the size of a tumor was measured at 2-3 day interval. Consequently, as shown in FIG. 8a, the combined treatment group of the anti-cancer drug and SP4 (a pool of combination 48 and 54) showed the significantly outstanding therapeutic effect than the combined treatment group of the anti-cancer drug and the pool of combination 44 and 51. It has been found that SP4 having a substituted residue in a base sequence showed better efficacy and effect than the siRNA pool of combination 44 and 51 having a unsubstituted residue in a base sequence. Moreover, as shown in FIG. 8b, when compared a size of tumors of a mouse of the anti-cancer agent administration group of cisplatin and paclitaxel with that of the combined treatment group of the anti-cancer agent and SP4 pool on day 17, it has been proven that there are large differences in the size and state. Also, as shown in FIG. 8c, a result obtained by observing amounts of variation in body weight of the mouse on day 9 and 28 showed no reduction in body weight caused by toxicity. Thus, it has been determined that there was no side effect caused by toxicity of siRNA.

Hitherto, specific features of the present invention are described in detail. However, it would be apparent to a person skilled in the art that the specific description is preferable embodiment only, and the scope of the invention is not limited thereto. Therefore, substantial scope of the present invention would be defined by accompanying claims and equivalents thereof.

The invention claimed is:

1. A method for preventing or treating a disease caused by HPV infection comprising:
   administering, to a subject, a pharmaceutical composition including:
   (a) a pharmaceutically effective amount of a nucleotide pool selected from the group consisting of:
   a pool of siRNA sequences comprising nucleotide sequences consisting of SEQ ID No: 2, nucleotide sequences consisting of SEQ ID No: 4, nucleotide sequences consisting of SEQ ID No: 8, nucleotide sequences consisting of SEQ ID No: 9, nucleotide sequences consisting of SEQ ID No: 12 and nucleotide sequences consisting of SEQ ID No: 15; or
   a pool of siRNA sequences comprising nucleotide sequences consisting of SEQ ID No: 58, nucleotide sequences consisting of SEQ ID No: 59, nucleotide sequences consisting of SEQ ID No: 63 and nucleotide sequences consisting of SEQ ID No: 65; and
   (b) a pharmaceutically acceptable carrier.

2. The method of claim 1, wherein the disease caused by HPV infection is selected from the group consisting of genital warts, vagina inflammation, pelvic inflammation and a cancer.

3. The method of claim 2, wherein the cancer is selected from the group consisting of cervical cancer, vagina cancer, vulva cancer, anal cancer, penis cancer, tonsil cancer, pharynx cancer, larynx cancer, head and neck cancer and lung adenocarcinoma.

4. The method of claim 1, wherein the pharmaceutical composition administered to the subject includes a pharmaceutically effective amount of a pool of siRNA sequences comprising nucleotide sequences consisting of SEQ ID No: 2, nucleotide sequences consisting of SEQ ID No: 4, nucleotide sequences consisting of SEQ ID No: 8, nucleotide sequences consisting of SEQ ID No: 9, nucleotide sequences consisting of SEQ ID No: 12 and nucleotide sequences consisting of SEQ ID No: 15.

* * * * *